(12) United States Patent
Tarby et al.

(10) Patent No.: US 7,125,895 B1
(45) Date of Patent: Oct. 24, 2006

(54) CYCLIC AMINE DERIVATIVES AND THEIR USES

(75) Inventors: Christine M. Tarby, Hockessin, DE (US); Wilna Moree, San Diego, CA (US)

(73) Assignee: Bristol-Myers Squibb Pharma Research Labs, Inc., Princeton, NJ (US)

( * ) Notice: Subject to any disclaimer, the term of this patent is extended or adjusted under 35 U.S.C. 154(b) by 0 days.

(21) Appl. No.: 09/569,766

(22) Filed: May 12, 2000

Related U.S. Application Data

(60) Provisional application No. 60/134,079, filed on May 14, 1999.

(51) Int. Cl.
| | |
|---|---|
| *A61K 31/4525* | (2006.01) |
| *A61K 31/4535* | (2006.01) |
| *C07D 211/32* | (2006.01) |
| *C07D 401/12* | (2006.01) |
| *C07D 405/12* | (2006.01) |

(52) U.S. Cl. ................. 514/315; 514/323; 514/326; 546/201; 546/213; 546/214; 546/245

(58) Field of Classification Search ............... 546/228
See application file for complete search history.

(56) References Cited

U.S. PATENT DOCUMENTS 4,895,842 A * 1/1990 Okamoto et al. ......... 514/227.5
5,643,946 A * 7/1997 Christensen, IV .......... 514/512

FOREIGN PATENT DOCUMENTS

| EP | 217 286 | 4/1987 |
|---|---|---|
| EP | 417 698 | 3/1991 |
| WO | WO 97/26250 | 7/1997 |
| WO | WO 98/04554 | 2/1998 |
| WO | WO 98/50534 | 11/1998 |
| WO | WO 99/00121 | 1/1999 |
| WO | WO 99/25686 | 5/1999 |

OTHER PUBLICATIONS

Flygare et al, Chemical Abstract vol. 131 No. 184944, Preparation of phenyl and aryl-fused thiazole derivatives as antiviral agents for suppression and treatment of herpes family viral infections and sexually-transmitted viral diseases. 1999.*

Flygare et al., STN International, HCAPLUS Database, Columbus, OH, Accession No. 1999:549264, Reg. No. 240136-65-6 (2006).*

Khalid et al., "N,N'-disubstituted L-isoglutamines as novel cancer chemotherapeutic agents," *Chemical Abstracts*, 107(7):16, abstract # 107, originally published in *Drugs Exp. Clin. Res.*, 13(1):57-60 (1987).

* cited by examiner

*Primary Examiner*—Kamal A. Saeed
*Assistant Examiner*—Andrew B. Freistein
(74) *Attorney, Agent, or Firm*—Mary K. VanAtten

(57) ABSTRACT

This invention relates to novel arylalkyl cyclic amine derivatives. This invention also relates to chemokine receptor antagonists that are be effective as therapeutic agents and/or preventive agents for diseases such as atherosclerosis, rheumatoid arthritis, transplant rejection, psoriasis, asthma, ulcerative colitis, glomerulonephritis, multiple sclerosis, pulmonary fibrosis, and myocarditis, in which tissue infiltration of blood monocytes and lymphocytes plays a major role in the initiation, progression or maintenance of the disease. Furthermore, chemokine receptor antagonists also inhibit the interaction of viruses, which attack blood monocytes and lymphocytes, through the use of a chemokine receptor. One such example is the HIV virus.

8 Claims, No Drawings

CYCLIC AMINE DERIVATIVES AND THEIR USES

CROSS-REFERENCES TO RELATED APPLICATIONS

This application claims priority to U.S. Provisional Patent Application No. 60/134,079, filed May 14, 1999.

FIELD OF THE INVENTION

This invention relates to novel arylalkyl cyclic amine derivatives. This invention also relates to chemokine receptor antagonists that are effective as therapeutic agents and/or preventive agents for diseases such as atherosclerosis, rheumatoid arthritis, transplant rejection, psoriasis, asthma, ulcerative colitis, glomerulonephritis, multiple sclerosis, pulmonary fibrosis, and myocarditis, in which tissue infiltration of blood monocytes and lymphocytes plays a major role in the initiation, progression or maintenance of the disease. Furthermore, chemokine receptor antagonists also inhibit the interaction of viruses, which attack blood monocytes and lymphocytes, through the use of a chemokine receptor. One such example is the HIV virus.

BACKGROUND OF THE INVENTION

Chemokines are a group of inflammatory/immunomodulatory polypeptide factors produced by lymphatic tissues and by activated macrophages and leukocytes at inflammatory sites; they have a molecular weight of 6–15 kD, contain four cysteine residues, are basic and have heparin binding activity. The chemokines can be classified into two subfamilies, the CXC chemokines and CC chemokines, by the common location of the four cysteine residues and by the differences in the chromosomal locations of the genes encoding them. For example IL-8 (abbreviation for interleukin-8) is a CXC chemokine, while the CC chemokines include MIP-1α/β (abbreviation for macrophage inflammatory protein-1α/β), MCP-1 (abbreviation for monocyte chemotactic protein-1), and RANTES (abbreviation for regulated on activation, normal T-cell expressed and secreted cytokine). There also exists a chemokine called lymphotactin, which does not fall into either chemokine subfamily. These chemokines promote cell migration, increase the expression of cellular adhesion molecules such as integrins, and promote cellular adhesion, and are thought to be the protein factors involved in the adhesion and infiltration of leukocytes into the pathogenic sites in inflammatory tissues (for references, see for example, Michiel, D., *Biotechnology*, 1993, 11, 739; Oppenheim, J. J., et al., *Annual Review of Immunology*, 1991, 9, 617–648; Schall, T. J., *Cytokine*, 1991, 3, 165–183; Springer, T. A., *Cell*, 1994, 76, 301–314; Furie, M. B., *American Journal of Pathology*, 1995, 146, 1287–1301; Kelner, G. S., et al., *Science*, 1994, 266, 1395–1399).

For example, MIP-1α induces cell migration and causes a transient increase in intracellular calcium ion concentration levels, an increase in the expression of integrins, and adhesion molecules, and degranulation of monocytes and lymphocytes, and inhibits bone marrow stem cell proliferation (See for example, Wolpe, S. D., et al., *Journal of Experimental Medicine*, 1988, 167, 570–581; Wolpe, S. D., et al., *Faseb Journal*, 1989, 3, 2565–2573; Taub, D. D., et al., *Science*, 1993, 260, 355–358; Schall, T. J., et al., *Journal of Experimental Medicine*, 1993, 177, 1821–1825; Neote, K., et al., *Cell*, 1993, 72, 415–425; Vaddi, K., et al.; *The Journal of Immunology*, 1994, 153, 4721–4732).

With respect to the activity of MIP-1α in vivo and its role in the pathogenesis of disease, it has been reported that it is a pyrogen in rabbits (see for example Davatelis, G., et al., *Science*, 1989, 243, 1066–1068); that MIP-1α injection into mouse foot pads results in an inflammatory reaction such as infiltration by neutrophils and mononuclear cells (see for example Alam, R., et al., *The Journal of Immunology*, 1994, 152, 1298–1303); that MIP-1α neutralizing antibody has an inhibitory effect or a therapeutic effect in animal models of granuloma, multiple sclerosis and idiopathic pulmonary fibrosis (see for example Lukacs, N. W., et al., *Journal of Experimental Medicine*, 1993, 177, 1551–1559; Karpus, W. J., et al., *The Journal of Immunology*, 1995, 155, 5003–5010; Smith, R. E., et al., *The Journal of Immunology*, 1994, 153, 4704–4712); and that coxsackie virus induced myocarditis is inhibited in mice with a disrupted MIP-1α gene (see for example Cook, D. N. et al., *Science*, 1995, 269, 1583–1585). These studies indicate that MIP-1 α is involved in the local attraction of various subtypes of leukocytes and the initiation, progression and maintenance of resulting inflammatory response.

These data indicate that chemokines, such as MIP-1α, attract monocytes and lymphocytes to disease sites and mediate their activation, and thus are involved in the initiation, progression and maintenance of diseases pertaining to monocytes and lymphocytes, such as atherosclerosis, rheumatoid arthritis, transplant rejection, psoriasis, asthma, ulcerative colitis, glomerulonephritis, multiple sclerosis, pulmonary fibrosis and myocarditis.

Therefore, drugs that inhibit the action of chemokines on target cells are effective as therapeutic and/or preventive drugs in diseases such as atherosclerosis, rheumatoid arthritis, transplant rejection, psoriasis, asthma, ulcerative colitis, glomerulonephritis, multiple sclerosis, pulmonary fibrosis, and myocarditis.

The chemokines bind specific cell-surface receptors belonging to the family of G-protein-coupled seven-transmembrane-domain proteins (reviewed in Horuk, *Trends Pharm. Sci.*, 15, 159–165 (1994)), which are termed "chemokine receptors." On binding their cognate ligands, chemokine receptors transduce an intracellular signal through the associated trimeric G protein, resulting in a rapid increase in intracellular calcium concentration. There are at least seven human chemokine receptors that bind or respond to CC-chemokines with the following characteristic pattern: CCR-1 (or "CKR-1" or "CC-CKR-1") [MIP-1α, MIP-β, MCP-3, RANTES] (Ben-Barroch, et al., *J. Biol. Chem.*, 270, 22123–22128 (1995), Beole, et al, *Cell*, 72, 416–426 (1993)); CCR-2A and CCR-2B (or "CKR-2A"/"CKR-2A" or "CC-CKR-2A:/:CC-CKR-2A") [MCP-1, MCP-3, MCP-4]; CCR-3 (or "CKR-3: or CC-CKR-3") [eotaxin, RANTES, MCP-3] (Combadiere, et at., *J. Biol. Chem.*, 270, 16491–16494 (1995); CCR-4 (or "CKR-4" or "CC-CKR-4") [MIP-1α, RANTES, MCP-1] (Power, et at., *J. Biol. Chem.*, 270, 19495–19500 (1995); CCR-5 (or "CKR-5" or "CC-CKR-5") [MIP-1α, RANTES, MIP-1β] (Sanson, et al., *Biochemistry*, 35, 3362–3367 (1996); and the Duffy bloodgroup antigen [RANTES, MCP-1] (Chaudhun, et al., *J. Biol. Chem.* 269, 7835–7838 (1994)).

Chemokine receptors, such as CCR-1, CCR-2, CCR-2A, CCR-2B, CCR-3, CCR-4, CCR-5, CXCR-3, CXCR-4, are considered important mediators of inflammatory and immunoregulatory disorders and diseases, including asthma and allergic diseases, as well as autoimmune pathologies such as rheumatoid arthritis and atherosclerosis. Accordingly, agents which modulate chemokine receptors would be useful in such disorders and diseases.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science,* 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophage-tropic viruses, which are believed to be the key pathogenic strains of HIV in vivo. It has recently been recognized that for efficient entry into target cells, human immunodeficiency viruses require the chemokine receptors CCR-5 and CXCR-4, as well as the primary receptor CD4 (Levy, N. *Engl. J. Med.,* 335(20), 1528–1530, (Nov. 14, 1996)). The principal cofactor for entry mediated by the envelope glycoproteins of primary macrophage-trophic strains of HIV-1 is CCR5, a receptor for the β-chemokines RANTES, MIP-1α and MIP-1β (Deng, et al., *Nature,* 381, 661–666 (1996)). HIV attaches to the CD4 molecule on cells through a region of its envelope protein, gp120. It is believed that the CD4 binding site on the gp120 of HIV interacts with the CD4 molecule on the cell surface, and undergoes conformational changes, which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that β-chemokine ligands prevent HIV-1 from fusing with the cell (Dragic, et al., *Nature* 381, 667–673 (1996)). It has further been demonstrated that a complex of gp120 and soluble CD4 interacts specifically with CCR-5 and inhibits the binding of the natural CCR-5 ligands MIP-1 α and MIP-1β (Wu, et al., *Nature* 384, 179–183 (1996); Trkola, et al., *Nature,* 384, 184–187 (1996)).

Humans who are homozygous for mutant CCR-5 receptors, which do not serve as co-receptors for HIV-1 in vitro, appear to be unusually resistant to HIV-1 infection and are not immunocompromised by the presence of this genetic variant (*Nature,* 332, 722–725 (1996)). Absence of CCR-5 appears to confer protection from HIV-1 infection (*Nature,* 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine,* 2(11), 1240–1243 (1996)). Nevertheless, drugs targeting chemokine receptors may not be unduly compromised by the genetic diversity of HIV-1 (Zhang, et al., *Nature,* 383, 766 (1996)). Accordingly, an agent that blocks chemokine receptors in humans who possess normal chemokine receptors should prevent infection in healthy individuals and slow or halt viral progression in infected patients. By focusing on the host's cellular immune response to HIV infection, better therapies towards all subtypes of HIV are provided. These results indicate that inhibition of chemokine receptors presents a method for the prevention or treatment of infection by HIV and the prevention or treatment of AIDS.

The peptides eotaxin, RANTES, MIP-1 α, MIP-1β, MCP-1, and MCP-3 are known to bind to chemokine receptors. As noted above, the inhibitors of HIV-1 replication present in supernatants of CD8+T cells have been characterized as the β-chemokines RANTES, MIP-1α and MIP-1β. Therefore, compounds that inhibit the binding of chemokines such as MIP-1α to these receptors, that is, chemokine receptor antagonists, are useful as drug targets that inhibit the action of chemokines on the target cells.

Recently, it was reported that the diphenylmethane derivatives (WO9724325) and other small molecules (WO9744329; WO9802151; WO9804554) are antagonists of chemokine receptors, such as the MIP-1α/RANTES receptor (defined as CCR1).

SUMMARY OF THE INVENTION

Therefore, the present invention provides small molecule compounds that inhibit the binding of chemokines, such as MIP-1α, to their receptors on the target cells and are useful in the prevention or treatment of certain inflammatory and immunoregulatory disorders and diseases, including asthma and allergic diseases, as well as autoimmune pathologies, such as rheumatoid arthritis and atherosclerosis. The invention is also directed to pharmaceutical compositions comprising these compounds and the use of these compounds and compositions in the prevention or treatment of such diseases in which chemokine receptors are involved.

The present invention is further concerned with compounds that inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

As a result of intensive studies, it was discovered that a series of cyclic amine compounds of Formula I and their pharmaceutically acceptable $C_1$–$C_6$ alkyl addition salts or their pharmaceutically acceptable acid addition salts inhibit the binding of chemokines, such as MIP-1α and the like, to the receptor of a target cell.

The present invention is a compound series of the formula (I) below:

Formula I

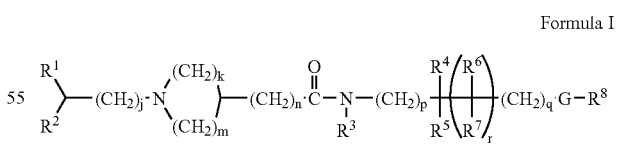

a pharmaceutically acceptable acid addition salt thereof or a pharmaceutically acceptable $C_1$–$C_6$ alkyl addition salt thereof, wherein $R^1$ is a phenyl group, a $C_3$–$C_8$ cycloalkyl group, or an aromatic heterocyclic group having 1–3 heteroatoms selected from the group consisting of an oxygen atom, a sulfur atom, and a nitrogen atom, or a combination thereof, in which the phenyl or aromatic heterocyclic group may be condensed with a benzene ring to form a condensed ring, and the phenyl group, $C_3$–$C_8$ cycloalkyl group, aromatic heterocyclic group, or condensed ring may be substituted with one or more of a halogen atom, a hydroxy group, a cyano group, a nitro group, a carboxy group, a carbamoyl group, a $C_1$–$C_6$ alkyl group, a $C_3$–$C_8$ cycloalkyl group, a $C_2$–$C_6$ alkenyl group, a $C_1$–$C_6$ alkoxy group, a $C_1$–$C_6$ alkylthio group, a $C_3$–$C_5$ alkylene group, a $C_2$–$C_4$ alkylenoxy group, a $C_1C_3$ alkylenedioxy group, a phenyl group, a phenoxy group, a phenylthio group, a benzyl group, a benzyloxy group, benzoylamino group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_4$–$C_9$ N-cycloalkylcarbamoyl group, a $C_1$–$C_6$ alkylsulfonyl group, a $C_3$–$C_8$ (alkoxycarbonyl)methyl group, a N-phenylcarbamoyl group, a piperidinocarbonyl group, a morpholinocarbonyl group, a 1-pyrrolidinylcarbonyl group, an amino group, a mono($C_1$–$C_6$ alkyl)amino group, or a di($C_1$–$C_6$ alkyl)amino group.

$R^2$ is a hydrogen atom, a $C_1$–$C_6$ alkyl group, a $C_2$–$C_7$ alkoxycarbonyl group, a hydroxy group, or a phenyl group, in which the $C_1$–$C_6$ alkyl or phenyl group may be substituted with one or more of a halogen atom, a hydroxy group, a $C_1$–$C_6$ alkyl group, or a $C_1$–$C_6$ alkoxy group, and when j=0, $R^2$ is not a hydroxy group.

In the formula, j represents an integer of 0–2;
k represents an integer of 0–2;
m represents an integer of 2–4; and
n represents an integer of 0–1.

$R^3$ is a hydrogen atom or a $C_1$–$C_6$ alkyl group optionally substituted with one or two phenyl groups each of which may be substituted with one or more of a halogen atom, a hydroxy group, a $C_1$–$C_6$ alkyl group, or a $C_1$–$C_6$ alkoxy group.

$R^4$ and $R^5$ are the same or different from each other and are a hydrogen atom, a hydroxy group, or a $C_1$–$C_6$ alkyl group, in which the $C_1$–$C_6$ alkyl group is optionally substituted with one or more of a halogen atom, a hydroxy group, a cyano group, a nitro group, a carboxy group, a carbamoyl group, a mercapto group, a guanidino group, a $C_3$–$C_8$ cycloalkyl group, a $C_1$–$C_6$ alkoxy group, a $C_1$–$C_6$ alkylthio group; a phenyl group optionally substituted with one or more of a halogen atom, a hydroxy group, a $C_1$–$C_6$ alkyl group, or a $C_1$–$C_6$ alkoxy group; a phenoxy group, a benzyloxy group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_1$–$C_6$ alkylsulfonyl group, an amino group, a mono($C_1$–$C_6$ alkyl)amino group, a di($C_1$–$C_6$ alkyl)amino group, or an aromatic heterocyclic group having 1–3 of heteroatoms selected from the group consisting of an oxygen atom, a sulfur atom, and a nitrogen atom, or a combination thereof, or $R^4$ and $R^5$ taken together form a 3 to 6 membered cyclic hydrocarbon;

$R^6$ and $R^7$ are the same or different from each other and are a hydrogen atom, a hydroxy group, or a $C_1$–$C_6$ alkyl group, in which the $C_1$–$C_6$ alkyl group is optionally substituted with one or more of a halogen atom, a hydroxy group, a cyano group, a nitro group, a carboxy group, a carbamoyl group, a mercapto group, a guanidino group, a $C_3$–$C_8$ cycloalkyl group, a $C_1$–$C_6$ alkoxy group, a $C_1$–$C_6$ alkylthio group; a phenyl group optionally substituted with one or more of a halogen atom, a hydroxy group, a $C_1$–$C_6$ alkyl group, or a $C_1$–$C_6$ alkoxy group; a phenoxy group, a benzyloxy group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_1$–$C_6$ alkylsulfonyl group, an amino group, a mono($C_1$–$C_6$ alkyl) amino group, a di($C_1$–$C_6$ alkyl)amino group, or an aromatic heterocyclic group having 1–3 of heteroatoms selected from the group consisting of an oxygen atom, a sulfur atom, and a nitrogen atom, or a combination thereof, or $R^6$ and $R^7$ taken together form a 3 to 6 membered cyclic hydrocarbon.

In the formula, p represents an integer of 0–1;
q represents an integer of 0–1; and
r represents an integer of 0–1.

G is a group represented by —CO—, —$SO_2$—, —CO—O—, —$NR^9$—CO—, —CO—$NR^9$—, —NH—CO—NH—, —NH—CS—NH—, —$NR^9$—$SO_2$—, —$SO_2$—$NR^9$—, —NH—CO—O—, or —O—CO—NH—, wherein $R^9$ is a hydrogen atom or a $C_1$–$C_6$ alkyl group, or $R^9$ taken together with $R^7$ represents $C_2$–$C_5$ alkylene group.

$R^8$ is a phenyl group, a $C_3$–$C_8$ cycloalkyl group, a $C_1$–$C_6$ alkoxy group, a $C_3$–$C_8$ cycloalkenyl group, a benzyl group, or an aromatic heterocyclic group having 1–3 heteroatoms selected from the group consisting of an oxygen atom, a sulfur atom, and a nitrogen atom, or a combination thereof, in which the phenyl, benzyl, or aromatic heterocyclic group may be condensed with a benzene ring or an aromatic heterocyclic group having 1–3 heteroatoms selected from the group consisting of an oxygen atom, a sulfur atom, and a nitrogen atom, or a combination thereof, to form a condensed ring, and the phenyl group, $C_3$–$C_8$ cycloalkyl group, $C_3$–$C_8$ cycloalkenyl group, benzyl group, aromatic heterocyclic group, or condensed ring may be substituted with one or more of a halogen atom, a hydroxy group, a mercapto group, a cyano group, a nitro group, a thiocyanato group, a carboxy group, an amido group, a carbamoyl group, a trifluoromethyl group, a $C_1$–$C_6$ alkyl group, a $C_3C_6$ cycloalkyl group, a $C_2$–$C_6$ alkenyl group, a $C_1$–$C_6$ alkoxy group, a $C_3$–$C_8$ cycloalkyloxy group, a $C_1$–$C_6$ alkylthio group, a $C_1$–$C_3$ alkylenedioxy group, a phenyl group, a phenoxy group, a phenylamino group, a benzyl group, a benzoyl group, a phenylsulfinyl group, a phenylsulfonyl group, a 3-phenylureido group, a $C_2$–$C_7$ alkanoyl group, a $C_2$–$C_7$ alkoxycarbonyl group, a $C_2$–$C_7$ alkanoyloxy group, a benzyloyloxy group, a $C_2$–$C_7$ alkanoylamino group, a $C_2$–$C_7$ N-alkylcarbamoyl group, a $C_1$–$C_6$ alkylsulfonyl group, a phenylcarbamoyl group, a N,N-di ($C_1$–$C_6$ alkyl)sulfamoyl group, an amino group, a mono($C_1$–$C_6$ alkyl)amino group, a di($C_1$–$C_6$ alkyl)amino group, a benzylamino group, a $C_2$–$C_7$ (alkoxycarbonyl) amino group, a $C_1$–$C_6$ (alkylsulfonyl) amino group, or a bis($C_1$–$C_6$ alkylsulfonyl)amino group.

More prefered are those compounds or salts, wherein $R^1$ is a phenyl group substituted with one or more of a halogen atom, a hydroxy group, a $C_1$–$C_6$ alkyl group, a $C_2$–$C_6$ alkoxy group, or an amino group; $R^2$ is a hydrogen atom, j=0, k=2, m=2, n=0, $R^3$ is a hydrogen atom, p=0 or 1, r=0, $R^4$ and $R^5$ are hydrogen atoms, q=0, G is —$NR^9$—CO—, —CO—, or O—CO—NH; and $R^8$ is a $C_1$–$C_6$ alkoxy group, a phenyl group or an aromatic hetercyclic group having 1–3 heteroatoms selected from the group consisting of an oxygen atom, a sulfur atom, and a nitrogen atom, or a combination thereof, in which the phenyl or aromatic heterocyclic group or condensed ring may be substituted with one or more of a halogen atom, a trifluoromethyl group, a $C_1$–$C_6$ alkylthio group, a $C_1$–$C_6$ alkoxy group, an amido group, a benzoyloxy group, a nitro group, a phenyl group, a cyano group, a $C_2$–$C_7$ alkanoyl group, or a $C_2$–$C_7$ alkanoylamino group.

The present invention includes a method for identifying a substance that competes for MIP-1α (Macrophage Inflammatory Protein) receptor binding comprising contacting a compound of claim 1 or a salt thereof, with MIP-1α and the substance, assaying the binding, and determining whether said substance competes for MIP-1α receptor binding.

Also described by this invention is a method of modulating chemokine receptor activity in a patient in need of such modulation comprising administering to the patient a therapeutically-effective amount of a compound of claim 1 or a salt thereof; and a method of treating an inflammatory or immunoregulatory disease in a patient in need of such treatment comprising administering to the patient a therapeutically-effective amount of a compound of claim 1 or a salt thereof. The diseases can be selected from the group consisting of transplant rejection, atherosclerosis, rheumatoid arthritis, psoriasis, asthma, ulcerative colitis, glomerulonephritis, multiple sclerosis, pulmonary fibrosis, and myocarditis.

Further, the invention describes a method of inhibiting the binding of human immunodeficiency virus to a chemokine receptor of a target cell comprising contacting the target cell with an amount of a compound of claim 1 or a salt thereof, sufficient to inhibit the binding; and a method of treating human immunodeficiency virus in a patient in need of such treatment comprising administering to the patient a thereapeutically-effective amount of a compound of claim 1 or a salt thereof.

Also, the present invention is a method of inhibiting the binding of a chemokine to the receptor of a target cell and/or its action on a target cell using a therapeutically effective amount of a compound represented by the above formula (I), a pharmaceutically acceptable acid addition salt thereof, or a pharmaceutically acceptable $C_1$–$C_6$ alkyl addition salt thereof.

The compounds represented by the above formula (I) inhibit the binding of chemokines, such as MIP-b 1α and the like, to the receptor of a target cell and inhibit physiological activities of cells caused by chemokines, such as MIP-1α and the like.

DESCRIPTION OF THE SPECIFIC EMBODIMENTS

Definitions

The "$C_3$–$C_8$ cycloalkyl group" means a cyclic alkyl group with three to eight carbon atoms, such as a cyclopropyl, cyclobutyl, cyclopentyl, cyclohexyl, cycloheptyl, and cyclooctyl group, preferably a cyclopropyl, cyclopentyl, or cyclohexyl group.

"Aromatic heterocyclic group having 1–3 heteroatoms selected from the group consisting of an oxygen atom, a sulfur atom, and a nitrogen atom, or a combination thereof" includes, for example, thienyl, furyl, pyrrolyl, imidazolyl, pyrazolyl, oxazolyl, isoxazolyl, thiazolyl, isothiazolyl, pryidyl, pyrimidinyl, triazinyl, triazolyl, oxadiazolyl, thiadiazolyl group or the like, preferably a thienyl, furyl, pyrrolyl, isoxazolyl, or pyridyl group.

"Condensed ring" means a ring obtained by the condensation with a benzene ring of a phenyl group or an aromatic heterocyclic group having 1–3 heteroatoms selected from the group consisting of an oxygen atom, a sulfur atom and/or a nitrogen atom, at any possible site, for example, naphthyl, indolyl, benzofuranyl, benzothienyl, quinolyl, benzimidazolyl, and benzotriazolyl groups.

"Halogen atom" means a fluorine atom, chlorine atom, bromine atom, or iodine atom, preferably a fluorine atom, chlorine atom, or bromine atom.

The "$C_1$–$C_6$ alkyl group" means a straight-chain or a branched alkyl group with one to six carbon atoms, such as a methyl, ethyl, n-propyl, n-butyl, n-pentyl, n-hexyl, n-heptyl, n-octyl, isopropyl, isobutyl, sec-butyl, tert-butyl, isopentyl, neopentyl, tert-pentyl, isohexyl, 2-methylpentyl, 1-ethylbutyl group, and the like, preferably a methyl, ethyl, or isopropyl group.

The "$C_2$–$C_6$ alkenyl group" means a straight-chain or a branched alkenyl group with two to six carbon atoms, such as a vinyl, allyl, 1-propenyl, 2-butenyl, 3-butenyl, 2-methyl-1-propenyl, 4-pentenyl, 5-hexenyl, 4-methyl-3-pentenyl group, and the like, preferably a vinyl or 2-methyl-1-propenyl group.

The "$C_3$–$C_8$ cycloalkenyl group" means a cyclic alkenyl group with three to eight carbon atoms, such as a cyclobutenyl, cyclopentenyl, cyclohexenyl, cycloheptenyl, and cyclooctenyl group, preferably a 2-cyclopentenyl or 1-cyclohexenyl group.

The "$C_1$–$C_6$ alkoxy group" means a group consisting of the aforementioned $C_1$–$C_6$ alkyl group and an oxy group, specifically, for example, a methoxy and ethoxy group.

The "$C_1$–$C_6$ alkylthio group" means a group consisting of the aforementioned $C_1$–$C_6$ alkyl group and a thio group, specifically, for example, a methylthio and ethylthio group.

The "$C_2$–$C_5$ alkylene group" consisting of $R^5$ or $R^7$, and $R^9$ means a straight-chain or branched alkylene group with two to five carbon atoms, such as a methylene, ethylene, propylene, trimethylene, tetramethylene, 1-methyltrimethylene, pentamethylene group, and the like, preferably a ethylene, trimethylene or tetramethylene group.

The "$C_3$–$C_5$ alkylene group" means a divalent alkylene group with three to five carbon atoms, such as a trimethylene, tetramethylene, pentamethylene, and 1-methyltrimethylene group, preferably, for example, a trimethylene or a tetramethylene group.

The "$C_2$–$C_4$ alkylenoxy group" means a $C_2$–$C_4$ divalent alkylene group substituted with an oxy group such as a ethylenoxy (—$CH_2CH_2O$—), trimethylenoxy (—$CH_2CH_2CH_2O$—), tetramethylenoxy (—$CH_2CH_2CH_2CH_2O$—), and 1,1-dimethylmethylenoxy (—$CH_2C(CH_3)_2O$—) group, preferably, for example, a ethylenoxy or trimethylenoxy group.

The "$C_1$–$C_3$ alkylenedioxy group" means a divalent alkylene group with one to three carbon atoms and substituted with two oxy groups, such as a methylenedioxy, ethylenedioxy, 1,3-propylenedioxy, and 1,2-propylenedioxy group, preferably, for example, a methylenedioxy or ethylenedioxy group.

The "$C_2$–$C_7$ alkanoyl group" means a straight-chain or branched alkanoyl group with two to seven carbon atoms, such as an acetyl, propanoyl, butanoyl, pentanoyl, hexanoyl, heptanoyl, isobutyryl, 3-methylbutanoyl, 3-methylbutanoyl, pivaloyl, 4-methylpentanoyl, 3,3-dimethylbutanoyl, 5-methylhexanoyl group, and preferably, for example, an acetyl group.

The "$C_2$–$C_7$ alkoxycarbonyl group" means a group consisting of the aforementioned $C_1$–$C_6$ alkoxy group and a carbonyl group, preferably, for example, a methoxycarbonyl or ethoxycarbonyl group.

The "$C_2$–$C_7$ alkanoyloxy group" means a group consisting of the aforementioned $C_2$–$C_7$ alkanoyl group and an oxy group, preferably, for example, an acetyloxy group.

The "$C_2$–$C_7$ alkanoylamino group" means a group consisting of the aforementioned $C_2$–$C_7$ alkanoyl group and an amino group, preferably, for example, an acetylamino group.

The "$C_2$–$C_7$ N-alkylcarbamoyl group" means a group consisting of the aforementioned $C_1$–$C_6$ alkyl group and a carbamoyl group, preferably, for example, a N-methylcarbamoyl or N-ethylcarbamoyl group.

The "$C_4$–$C_9$ N-cycloalkylcarbamoyl group" means a group consisting of the aforementioned $C_3$–$C_8$ cycloalkyl group and a carbamoyl group, preferably, for example, a N-cyclopentylcarbamoyl or N-cyclohexylcarbamoyl group.

The "$C_1$–$C_6$ alkylsulfonyl group" means a group consisting of the aforementioned $C_1$–$C_6$ alkyl group and a sulfonyl group, preferably, for example, a methylsulfonyl group.

The "$C_3$–$C_8$ (alkoxycarbonyl) methyl group" means a group consisting of the aforementioned $C_2$–$C_7$ alkoxycarbonyl group and a methyl group, preferably, for example, a (methoxycarbonyl) methyl or (ethoxycarbonyl) methyl group.

The "mono ($C_1$–$C_6$ alkyl) amino group" means an amino group substituted with one of the aforementioned $C_1$–$C_6$ alkyl group, preferably, for example, a methylamino or ethyl amino group.

The "di ($C_1$–$C_6$ alkyl) amino group" means an amino group substituted with two of the same or different aforementioned $C_1$–$C_6$ alkyl groups, preferably, for example, a dimethylamino, diethylamino, or N-ethyl-N-methylamino group.

The "$C_3$–$C_8$ cycloalkyloxy group" means a group consisting of the aforementioned $C_3$–$C_8$ cycloalkyl group and an oxy group, specifically, for example, a cyclopropyloxy, cyclopentyloxy, and cyclohexyloxy group.

The "$C_2$–$C_7$ (alkoxycarbonyl) amino group" means a group consisting of the aforementioned $C_2$–$C_7$ alkoxycarbonyl group and an amino group, specifically, for example, a ($C_2$ methoxycarbonyl) amino and (ethoxycarbonyl) amino group.

The "N,N-di ($C_1$–$C_6$ alkyl) sulfamoyl group" means a sulfamoyl group substituted with two of the same or different aforementioned $C_1$–$C_6$ alkyl groups, preferably and specifically, for example, a N,N-dimethylsulfamoyl, N,N-diethylsulfamoyl, or N-ethyl-N-methylsulfamoyl group.

The "$C_1$–$C_6$ (alkylsulfonyl) amino" group means a group consisting of the aforementioned $C_1$–$C_6$ alkylsulfonyl group and an amino group, specifically, for example, a (methylsulfonyl) amino group.

The "bis ($C_1$–$C_6$ alkylsulfonyl) amino" group means an amino group substituted with two of the same or different aforementioned $C_1$–$C_6$ alkyl groups, specifically, for example, a bis (methylsulfonyl) amino group.

For the purposes of these definitions, all groups can be further substituted by various applicable groups, and the definitions shall be considered to include such substitutions.

In the above formula (I), $R^1$ is a phenyl group, a $C_3$–$C_8$ cycloalkyl group, or an aromatic heterocyclic group having 1–3 heteroatoms selected from the group consisting of an oxygen atom, a sulfur atom, and a nitrogen atom, or a combination thereof, in which the phenyl or aromatic heterocyclic group may be condensed with a benzene ring to form a condensed ring, and the phenyl group, $C_3$–$C_8$ cycloalkyl group, aromatic heterocyclic group, or condensed ring may be substituted with one or more of a halogen atom, a hydroxy group, a cyano group, a nitro group, a carboxy group, a carbamoyl group, a $C_1$–$C_6$ alkyl group, a $C_3$–$C_8$ cycloalkyl group, a $C_2$–$C_6$ alkenyl group, a $C_1$–$C_6$ alkoxy group, a $C_1$–$C_6$ alkylthio group, a $C_3$–$C_5$ alkylene group, a $C_2$–$C_4$ alkylenoxy group, a $C_1$–$C_3$ alkylenedioxy group, a phenyl group, a phenoxy group, a phenylthio group, a benzyl group, a benzyloxy group, a benzoylamino group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_4$–$C_9$ N-cycloalkylcarbamoyl group, a $C_1$–$C_6$ alkylsulfonyl group, a $C_3$–$C_8$ (alkoxycarbonyl)methyl group, a N-phenylcarbamoyl group, a piperidinocarbonyl group, a morpholinocarbonyl group, a 1-pyrrolidinylcarbonyl group, an amino group, a mono ($C_1$–$C_6$ alkyl)amino group, or a di ($C_1$–$C_6$ alkyl)amino group.

In the above formula (I), $R^2$ represents a hydrogen atom, a $C_1$–$C_6$ alkyl group, a $C_2$–$C_7$ alkoxycarbonyl group, a hydroxy group, or a phenyl group, in which the $C_1$–$C_6$ alkyl or phenyl group may be substituted with one or more of a halogen atom, a hydroxy group, a $C_1$–$C_6$ alkyl group, or a $C_1$–$C_6$ alkoxy group, and when j=0, $R^2$ is not a hydroxy group.

In the above formula (I), j represents an integer of 0, 1, or 2.

In the above formula (I), k represents an integer of 0, 1, or 2 and m represents an integer of 2, 3, or 4. It is preferred to use a 2-substituted pyrrolidine in which k is 0 and m is 3, a 3-substituted pyrrolidine in which k is 1 and m is 2, a 3-substituted piperidine in which k is 1 and m is 3, a 4-substituted piperidine in which k is 2 and m is 2, or 3-substituted hexahydroazepine in which k is I and m is 4.

n in the above formula (I) represents an integer of 0 or 1.

$R^3$ in the above formula (I) represents a hydrogen atom or a $C_1$–$C_6$ alkyl group optionally substituted with one or two phenyl groups each of which may be substituted with one or more of a halogen atom, a hydroxy group, a $C_1$–$C_6$ alkyl group, or a $C_1$–$C_6$ alkoxy group.

In the above formula (1), $R^4$ and $R^5$ are the same or different from each other and are a hydrogen atom, a hydroxy group, or a $C_1$–$C_6$ alkyl group, in which the $C_1$–$C_6$ alkyl group is optionally substituted with one or more of a halogen atom, a hydroxy group, a cyano group, a nitro group, a carboxy group, a carbamoyl group, a mercapto group, a guanidino group, a $C_3$–$C_8$ cycloalkyl group, a $C_1$–$C_6$ alkoxy group, a $C_1$–$C_6$ alkylthio group; a phenyl group optionally substituted with one or more of a halogen atom, a hydroxy group, a $C_1$–$C_6$ alkyl group, or a $C_1$–$C_6$ alkoxy group; a phenoxy group, a benzyloxy group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_1$–$C_6$ alkylsulfonyl group, an amino group, a mono ($C_1$–$C_6$ alkyl) amino group, a di ($C_1$–$C_6$ alkyl) amino group, or an aromatic heterocyclic group having 1–3 of heteroatoms selected from the group consisting of an oxygen atom, a sulfur atom, and a nitrogen atom, or a combination thereof, or $R^4$ and $R^5$ taken together form a 3 to 6 membered cyclic hydrocarbon.

The "3 to 6 membered cyclic hydrocarbon" consisting of $R^4$, $R^5$, and the adjacent carbon atom, such as cyclopropane, cyclobutane, cyclopentane, or cyclohexane.

In the above formula (I), $R_6$ and $R_7$ are the same or different from each other and are a hydrogen atom, a hydroxy group, or a $C_1$–$C_6$ alkyl group, in which the $C_1$–$C_6$ alkyl group is optionally substituted with one or more of a halogen atom, a hydroxy group, a cyano group, a nitro group, a carboxy group, a carbamoyl group, a mercapto group, a guanidino group, a $C_3$–$C_8$ cycloalkyl group, a $C_1$–$C_6$ alkoxy group, a $C_1$–$C_6$ alkylthio group; a phenyl group optionally substituted with one or more of a halogen atom, a hydroxy group, a $C_1$–$C_6$ alkyl group, or a $C_1$–$C_6$ alkoxy group; a phenoxy group, a benzyloxy group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_1$–$C_6$ alkylsulfonyl group, an amino group, a mono($C_1$–$C_6$ alkyl)amino group, a di($C_1$–$C_6$ alkyl)amino group, or an aromatic heterocyclic group having 1–3 of heteroatoms selected from the group consisting of an oxygen atom, a sulfur atom, and a nitrogen atom, or a combination thereof, or $R^6$ and $R^7$ taken together form a 3 to 6 membered cyclic hydrocarbon.

In the above formula (I), p represents an integer of 0 or 1, q represents an integer of 0 or 1 and r represents an integer of 0 or 1.

In the above formula (I), G is a group represented by —CO—, $SO_2$—, —CO—O—, $NR^9$—CO—, —CO—$NR^9$—, —NH—CO—NH—, —NH—CS—NH, —$NR^9SO_2$—, —$SO_2$—$NR^9$—, —NH—CO—O—, or —O—CO—NH—, wherein $R^9$ is a hydrogen atom or a $C_1$–$C_6$ alkyl group, or $R^9$ taken together with $R^7$ represents a $C_2$–$C_5$ alkylene group.

In the above formula, —CO— means a carbonyl group, —$SO_2$— means a sulfonyl group, and —CS— means a thiocarbonyl group.

In the above formula (I), $R^8$ is a phenyl group, a $C_3$–$C_8$ cycloalkyl group, a $C_3$–$C_8$ cycloalkenyl group, a benzyl group, or an aromatic heterocyclic group having 1–3 heteroatoms selected from the group consisting of an oxygen atom, a sulfur atom, and a nitrogen atom, or a combination thereof, in which the phenyl, benzyl, or aromatic heterocyclic group may be condensed with a benzene ring or an aromatic heterocyclic group having 1–3 heteroatoms selected from the group consisting of an oxygen atom, a sulfur atom, and a nitrogen atom, or a combination thereof, to form a condensed ring, and the phenyl group, $C_3$–$C_8$ cyclalkyl group, $C_3$–$C_8$ cycloalkenyl group, benzyl group, aromatic heterocyclic group, or condensed ring may be substituted with one or more of a halogen atom, a hydroxy group, a mercapto group, a cyano group, a nitro group, a thiocyanato group, a carboxy group, a carbamoyl group, a trifluoromethyl group, a $C_1$–$C_6$ alkyl group, a $C_3$–$C_6$ cycloalkyl group, a $C_2$–$C_6$ alkenyl group, a $C_1$–$C_6$ alkoxy group, a $C_3$–$C_8$ cycloalkyloxy group, a $C_1$–$C_6$ alkylthio group, a $C_1$–$C_3$ alkylenedioxy group, a phenyl group, a phenoxy group, a phenylamino group, a benzyl group, a benzoyl group, a phenylsulfinyl group, a phenylsulfonyl group, a 3-phenylureido group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_1$–$C_6$ alkylsulfonyl group, a phenylcarbamoyl group, a N,N-di ($C_1$–$C_6$ alkyl) sulfamoyl group, an amino group, a mono ($C_1$–$C_6$ alkyl) amino group, a di ($C_1$–$C_6$ alkyl) amino group, a benzylamino group, a $C_2$–$C_7$ (alkoxycarbonyl) amino group, a $C_1$–$C_6$ (alkylsulfonyl) amino group, or a bis ($C_1$–$C_6$ alkylsulfonyl) amino group.

A halogen atom, a mercapto group, a nitro group, a thiocyanato group, a trifluoromethyl group, a $C_1$–$C_6$ alkyl group, a $C_1$–$C_6$ alkoxy group, a phenyl group, a phenylsulfonyl group, a $C_2$–$C_7$ alkanoylamino group, or an amino group is a preferred substituent for the phenyl group, $C_3$–$C_8$ cycloalkyl group, $C_3$–$C_8$ cycloalkenyl group, benzyl group, aromatic heterocyclic group, or condensed ring in $R^8$.

Furthermore, the phenyl group, $C_3$–$C_8$ cycloalkyl group, $C_3$–$C_8$ cycloalkenyl group, benzyl group, aromatic heterocyclic group, or condensed ring in $R^8$ can be optionally substituted with one or more of a halogen atom, a cyano group, a hydroxy group, an amino group, trifluoromethyl group, a $C_1$–$C_6$ alkyl group, a $C_1$–$C_6$ alkoxy group, a $C_1$–$C_6$ alkylthio group, a mono ($C_1$–$C_6$ alkyl) amino group, or a di ($C_1$–$C_6$ alkyl)amino group.

The compounds represented by the formula (I) above, a pharmaceutically acceptable acid addition salt thereof or a pharmaceutically acceptable $C_1$–$C_6$ alkyl addition salt can be used as a chemokine receptor antagonist by formulating a therapeutically-effective amount of the compound with a carrier and/or diluent into a pharmaceutical composition. Thus, the cyclic amine derivatives shown by the above formula (I) or their salts can be administered orally or parenterally, for example, intravenously, subcutaneously, intramuscularly, percutaneously or intrarectally.

Pharmaceutical compositions comprising the claimed compounds are useful for the treatment of diseases such as rheumatoid arthritis. The antagonist is administered as a pharmaceutical composition comprising a therapeutically effective amount of the compound and a pharmaceutically acceptable vehicle. Such pharmaceutical compositions may also contain pharmaceutically acceptable carriers, diluents, fillers, salts, buffers, stabilizers and/or other materials well-known in the art. The term "pharmaceutically acceptable" means a material that does not interfere with the effectiveness of the biological activity of the active ingredient(s) and that is not toxic to the host to which it is administered. The characteristics of the carrier or other material will depend on the route of administration.

Administration can be carried out in a variety of conventional ways. (See (1996) *Goodman's and Gilman's: The Pharmacological Bases of Therapeutics* ($9^{th}$ ed.) Pergamon Press; and (1990) *Remington's Pharmaceutical Sciences* ($17^{th}$ ed.) Mack Publishing Co.) Parenteral administration is preferred. In such cases, the composition may be in the form of a non-pyrogenic, sterile, parenterally acceptable aqueous solution. The preparation of such parenterally acceptable solutions, having due regard to pH, isotonicity, stability and the like, is within the skill in the art. In the long term, however, oral administration will be advantageous, since it is expected that the active compositions will be used over a long time period to treat chronic conditions.

The amount of active ingredient will depend upon the severity of the condition, the route of administration, the activity of the compound, and ultimately will be decided by the attending physician. It is currently contemplated, however, that the various pharmaceutical compositions should contain about 10 micrograms to about 1 milligram per milliliter of compound.

In practicing the method of treatment of this invention, a therapeutically effective amount of the composition is administered to a human patient in need of such treatment. The term "therapeutically effective amount" means the total amount of the active component of the method or composition that is sufficient to show a meaningful patient benefit, i.e., healing of chronic conditions or increase in rate of healing. A therapeutically effective dose of a composition of this invention is contemplated to be in the range of about 10 micrograms to about 1 milligram per milliliter per dose administered. The number of doses administered may vary, depending on the individual patient and the severity of the condition.

The oral administration can be accomplished in the form of tablets, pills, granules, powder, solution, suspension, capsules, etc. The tablets can be prepared using a vehicle, such as lactose, starch and crystallized cellulose; a binder such as carboxymethylcellulose, methylcellulose, and polyvinylpyrrolidone; a disintegrator such as sodium alginate, sodium bicarbonate and sodium lauryl sulfate, etc.

Pills, powder and granule preparations can be prepared by standard methods using the vehicles mentioned above. A solution or suspension can be prepared by standard methods using a glycerin ester, such as tricaprylin and triacetin, or an alcohol, such as ethanol. Capsules can be made by charging granules, powder or solution in gelatin, etc.

Subcutaneous, intramuscular or intravenous preparations can be prepared as an injection using an aqueous or non-aqueous solution. An aqueous solution for example, may include isotonic sodium chloride solution. Nonaqueous solutions may include for example, propyleneglycol, polyethyleneglycol, olive oil, ethyl oleate, etc., and optionally, one can add antiseptics and stabilizers. For injection, the preparation can be sterilized by filtration through a bacterial filter or a combination of disinfectants.

Percutaneous administration may use an ointment or cream, and ointment can be prepared using fatty oils, such as castor oil and olive oil, while creams can be made using fatty oils or emulsifying agents, such as diethyleneglycol and sorbitan esters of fatty acid.

For intrarectal administration, one can use standard suppositories, such as gelatin soft capsules, etc.

The cyclic amine derivatives of the present invention, pharmaceutically acceptable acid addition salts thereof or pharmaceutically acceptable $C_1$–$C_6$ alkyl addition salts are administered at a dose depending on the type of disease, route of administration, age and sex of patient, and severity of disease, but is likely to be 1–500 milligrams (mg)/day in an average adult.

These small molecule compounds, which inhibit the binding of chemokines such as MIP-1α to their receptors on the target cells, are useful in the prevention or treatment of certain inflammatory and immunoregulatory disorders and diseases, including asthma and allergic diseases, as well as autoimmune pathologies such as rheumatoid arthritis, and multiple sclerosis. The invention is also directed to pharmaceutical compositions comprising these compounds and the use of these compounds and compositions in the prevention or treatment of such diseases in which chemokine receptors are involved.

The present invention is further concerned with compounds that inhibit the entry of human immunodeficiency virus (HIV) into target cells and are used in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

As described in the Background Section, the novel compounds of this invention can be particularly utilized for atherosclerosis, rheumatoid arthritis, transplant rejection, psoriasis, asthma, ulcerative colitis, glomerulonephritis, multiple sclerosis, pulmonary fibrosis and myocarditis. Further, the compounds of this invention inhibit the binding of human MIP-1α (Macrophage Inflammatory Protein) to THP-1 cells and thereby affect those diseases relating to monocytes and lymphocytes and their activation. One of skill in the art would appreciate the therapeutic value of an antagonist to MIP-1α or its receptor, wherein the compounds of formula (I) interfere with this interaction. A number of therapeutic compounds that are CCR1 or CCR5 antagonists have been described previously. (See Saunders, et al., *Drug Discovery Today*, 1999, 4(2) 80–91 and Horuk, et al., *Medicinal Research Review*, 2000, 20, 155–168).

The subject compounds are useful in a method of modulating chemokine receptor activity in a patient in need of such modulation comprising the administration of a therapeutically effective amount of the compound.

The present invention is directed to the use of the foregoing compounds as modulators of chemokine receptor activity. In particular, these compounds are useful as modulators of the chemokine receptors, including CCR-1, CCR-4, and/or CCR-5.

The utility of the compounds in accordance with the present invention as modulators of chemokine receptor activity may be demonstrated by methodology known in the art, such as the assay for CCR-1 and/or CCR-5 binding as disclosed by Van Riper, et al., *J. Exp. Med.*, 177, 851–856 (1993), and the assay for CCR-2 and/or CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, or HEK-293. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

Mammalian chemokine receptors provide a target for interfering with or promoting lymphocyte function in a mammal, such as a human. Compounds which inhibit or promote chemokine receptor function, are particularly useful for modulating monocytes and/or lymphocyte function for therapeutic purposes. Accordingly, the present invention is directed to compounds, which are useful in the prevention and/or treatment of a wide variety of inflammatory and immunoregulatory disorders and diseases, including asthma and allergic diseases, as well as autoimmune pathologies such as rheumatoid arthritis and atherosclerosis.

Similarly, an instant compound that promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes.

In addition to primates, such as humans, a variety of other mammals can be treated according to the methods of the present invention. For instance, mammals including, but not limited to, cows, sheep, goats, horses, dogs, cats, guinea pigs, rats or other bovine, ovine, equine, canine, feline, rodent or murine species can be treated. However, the methods can also be practiced on other species, such as avian species (e.g., chickens).

Diseases and conditions associated with inflammation and infection can be treated using the methods of the present invention. In a preferred embodiment, the disease or condition is one in which the actions of lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thryoiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, and dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic disease, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticerocis); visceral worms, visceral larva migrans (e.g., Toxocara), eosinophilic gastroenteritis (e.g., *Anisaki* spp., *Phocanema* ssp.), cutaneous larva migrans (*Ancylostona brasiliense, Ancylostoma caninum*).

The compounds of the present invention are accordingly useful in the prevention and treatment of a wide variety of inflammatory and immunoregulatory disorders and diseases.

In another aspect, the instant invention may be used to evaluate putative specific agonists or antagonists of chemokine receptors. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of bodily fluids, bites, accidental needle stick, or exposure to patient blood during surgery. In addition, a compound of the present invention may be used for the prevention of infection by HIV and the prevention of AIDS, such as in post-coital prophylaxis or in the prevention of maternal transmission of the HIV virus to a fetus or a child upon birth.

In a preferred aspect of the present invention, a subject compound may be used in a method of inhibiting the binding of a human immunodeficiency virus to a chemokine receptor of a target cell, which comprises contacting the target cell with the amount of the compound that is effective at inhibiting the binding of the virus to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism and/or partial agonism. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and/or "administering a" compound should be understood to mean providing a compound of the invention or a prodrug of a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent, such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, fentanyl, ibuprofen, indomethacin, ketorolac, morphine, naproxen, phenacetin, piroxican, a steroidal analgesic, sufentanyl, sulindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophendrine, oxymetazoline, ephinephrine, naphazoline, xylometazoline, propylhexedrine, or levodesoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) idinavir with efavirenz, and, optionally, AZT and/or 3TC and/or ddI and/or ddC; (2) indinavir, and any of AZT and/or ddI and/or ddC and/or 3TC, in particular, indinavir and AST and 3TC; (3) stavudine and 3TC and/or zidovudine; (4) zidovudine and lamivudine and 141W94 and 1592U89; (5) zidovudine and lamuvidine.

In such combinations the compound of the present invention and other active agents may be administered separately or in conjunction. In addition, the administration of one element may be prior to, concurrent to, or subsequent to the administration of other agent(s).

Preferred specific examples for the cyclic amine compounds in the above formula (I) include compounds having each substituent as shown in the following Table 1.

In Table 1, "chirality" means configuration of the asymmetric carbon atom on the cyclic amine. "R" shows that the asymmetric carbon atom has an R configuration, "S" shows that the asymmetric carbon atom has a S configuration, and "-" means the racemate or that the compound does not have an asymmetric carbon atom on the nitrogen containing ring.

TABLE 1

| Compound No. | $R^1R^2CH(CH_2)_j$— | k | m | n | Chiral | R3 | $(CH_2)_p$—[$R^4R^5$]—[$R^6R^7$]$_r$—$(CH_2)_q$—G—$R^8$ |
|---|---|---|---|---|---|---|---|
| 1 | Cl—C6H4—CH2— | 2 | 2 | 0 | — | H | —(CH2)2—NH—C(O)—C6H5 |
| 2 | Cl—C6H4—CH2— | 2 | 2 | 0 | — | H | —(CH2)2—NH—C(O)—C6H4-3-CF3 |
| 3 | Cl—C6H4—CH2— | 2 | 2 | 0 | — | H | —(CH2)2—NH—C(O)—C6H4-3-CF3 |
| 4 | Cl—C6H4—CH2— | 2 | 2 | 0 | — | H | —(CH2)2—NH—C(O)—C6H4-3-SO2CH3 |
| 5 | Cl—C6H4—CH2— | 2 | 2 | 0 | — | H | —(CH2)2—NH—C(O)—C6H4-3-Br |
| 6 | Cl—C6H4—CH2— | 2 | 2 | 0 | — | H | —(CH2)2—NH—C(O)—C6H4-3-Cl |

TABLE 1-continued
| Compound No. | R¹, R², (CH₂)ⱼ | k | m | n | Chiral | R3 | (CH₂)ₚ, R⁴, R⁵, R⁶, R⁷, (CH₂)_q—G—R⁸ |
|---|---|---|---|---|---|---|---|
| 7 | 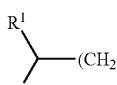 | 2 | 2 | 0 | — | H | 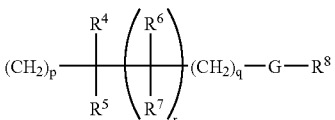 |
| 8 | 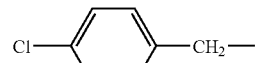 | 2 | 2 | 0 | — | H | 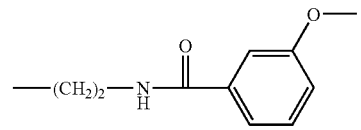 |
| 9 | 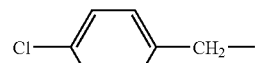 | 2 | 2 | 0 | — | H | 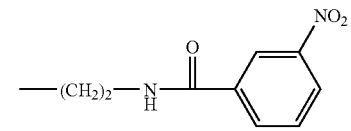 |
| 10 | 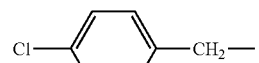 | 2 | 2 | 0 | — | H | 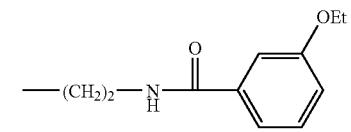 |
| 11 | 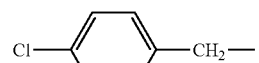 | 2 | 2 | 0 | — | H | 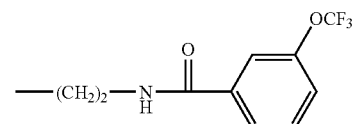 |
| 12 | 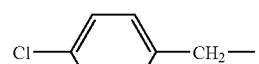 | 2 | 2 | 0 | — | H | 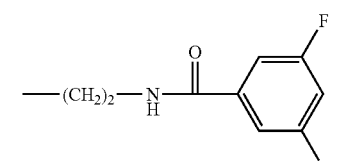 |
| 13 | 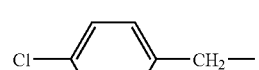 | 2 | 2 | 0 | — | H | 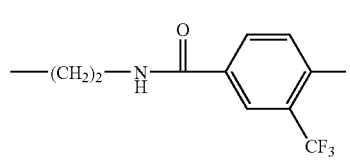 |
| 14 | 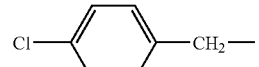 | 2 | 2 | 0 | — | H | 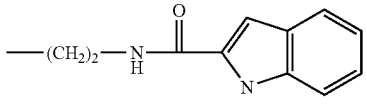 |
| 15 | 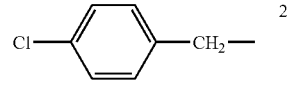 | 2 | 2 | 0 | — | H | 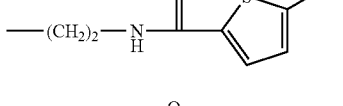 |
| 16 | 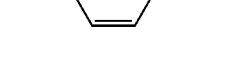 | 2 | 2 | 0 | — | H | 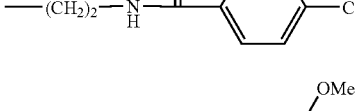 |

TABLE 1-continued
| Compound No. | R¹ R² (CH₂)ⱼ | k | m | n | Chiral | R3 | (CH₂)ₚ [R⁴/R⁵] ([R⁶/R⁷])ᵣ (CH₂)q—G—R⁸ |
|---|---|---|---|---|---|---|---|
| 17 | 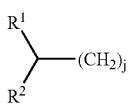 | 2 | 2 | 0 | — | H | 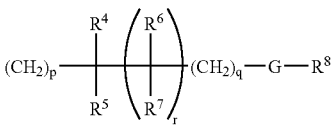 |
| 18 | 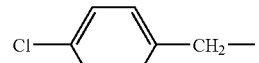 | 2 | 2 | 0 | — | H | 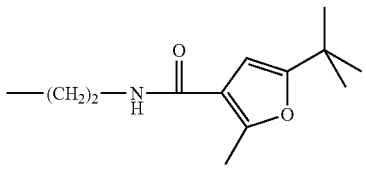 |
| 19 | 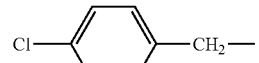 | 2 | 2 | 0 | — | H | 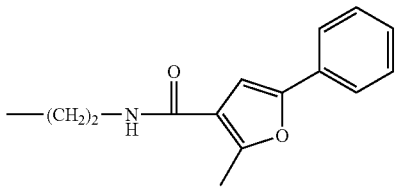 |
| 20 | 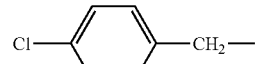 | 2 | 2 | 0 | — | H | 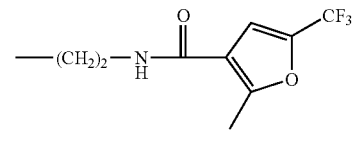 |
| 21 | 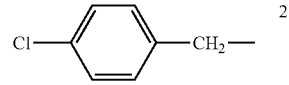 | 2 | 2 | 0 | — | H | 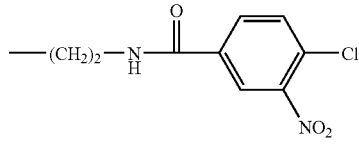 |
| 22 | 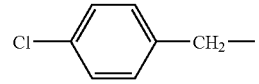 | 2 | 2 | 0 | — | H | 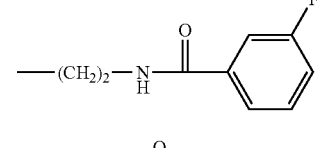 |
| 23 | 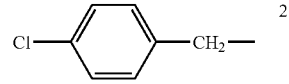 | 2 | 2 | 0 | — | H | 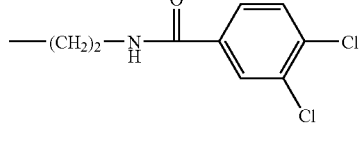 |
| 24 | 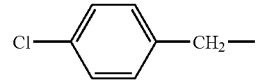 | 2 | 2 | 0 | — | H | 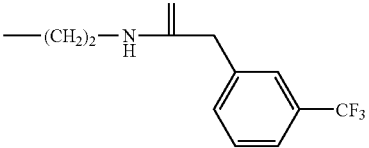 |
| 25 | 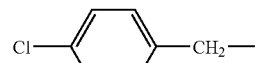 | 2 | 2 | 0 | — | H | 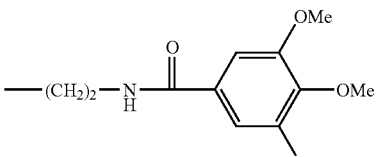 |

TABLE 1-continued
| Compound No. | R¹, R², (CH₂)ⱼ group | k | m | n | Chiral | R3 | (CH₂)p, R⁴, R⁵, (R⁶, R⁷)r, (CH₂)q—G—R⁸ group |
|---|---|---|---|---|---|---|---|
| 26 | 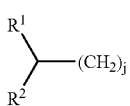 | 2 | 2 | 0 | — | H | 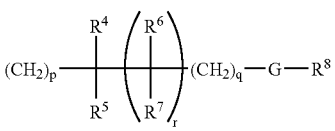 |
| 27 | 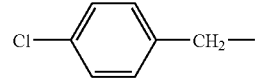 | 2 | 2 | 0 | — | H | 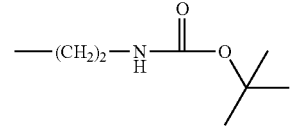 |
| 28 | 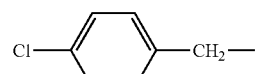 | 2 | 2 | 0 | — | H | 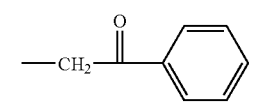 |
| 29 | 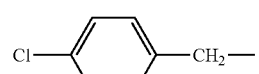 | 2 | 2 | 0 | — | H | 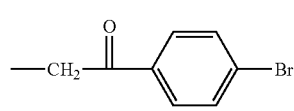 |
| 30 | 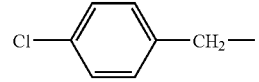 | 2 | 2 | 0 | — | H | 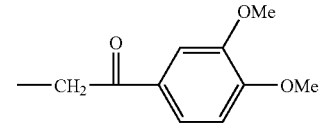 |
| 31 | 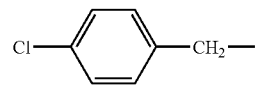 | 2 | 2 | 0 | — | H | 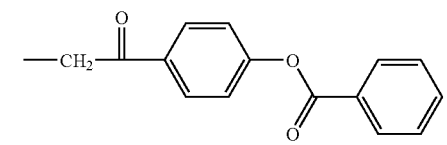 |
| 32 | 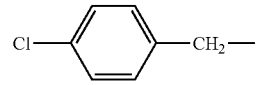 | 2 | 2 | 0 | — | H | 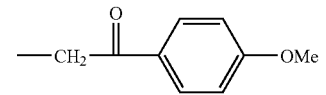 |
| 33 | 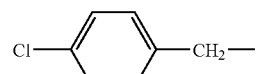 | 2 | 2 | 0 | — | H | 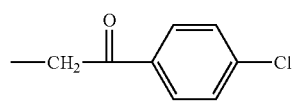 |
| 34 | 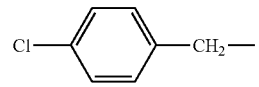 | 2 | 2 | 0 | — | H | 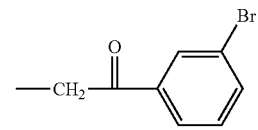 |
| 35 | 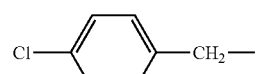 | 2 | 2 | 0 | — | H | 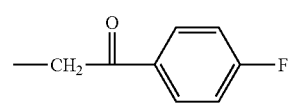 |
| 36 | 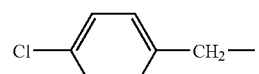 | 2 | 2 | 0 | — | H | 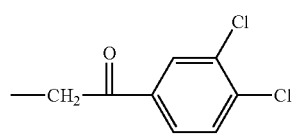 |

TABLE 1-continued
| Compound No. | 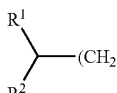 | k | m | n | Chiral | R3 | 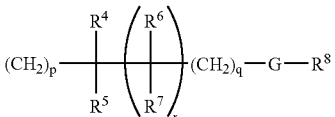 |
|---|---|---|---|---|---|---|---|
| 37 | 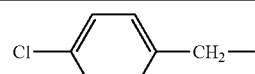 | 2 | 2 | 0 | — | H | 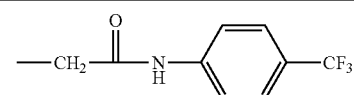 |
| 38 | 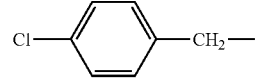 | 2 | 2 | 0 | — | H | 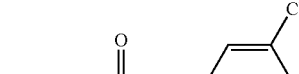 |
| 39 | 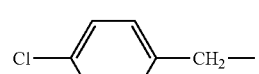 | 2 | 2 | 0 | — | H | 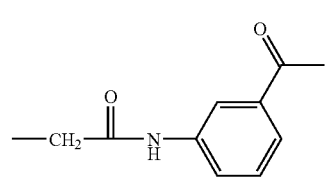 |
| 40 | 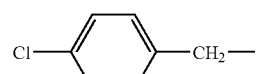 | 2 | 2 | 0 | — | H | 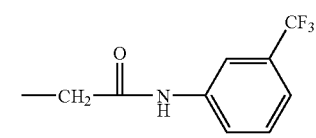 |
| 41 | 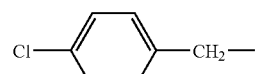 | 2 | 2 | 0 | — | H | 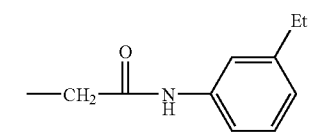 |
| 42 | 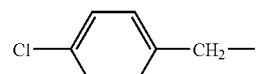 | 2 | 2 | 0 | — | H | 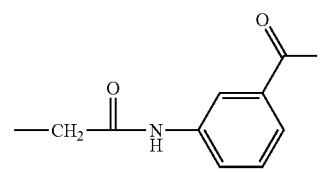 |
| 43 | 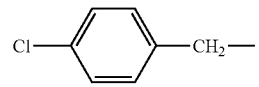 | 2 | 2 | 0 | — | H | 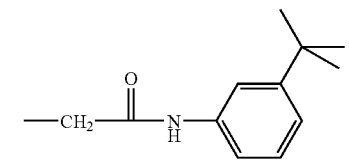 |
| 44 | 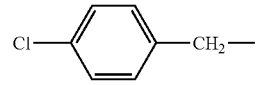 | 2 | 2 | 0 | — | H | 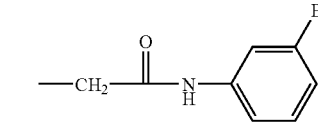 |
| 45 | 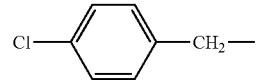 | 2 | 2 | 0 | — | H | 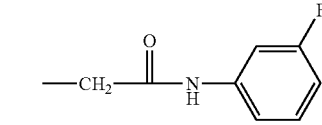 |
| 46 | 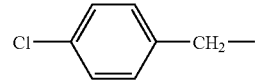 | 2 | 2 | 0 | — | H | 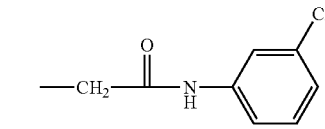 |

TABLE 1-continued

| Compound No. | R¹, R², (CH₂)ⱼ | k | m | n | Chiral | R3 | (CH₂)ₚ–[R⁴,R⁵]–([R⁶,R⁷])ᵣ–(CH₂)q–G–R⁸ |
|---|---|---|---|---|---|---|---|
| 47 | 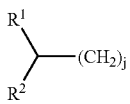 | 2 | 2 | 0 | — | H | 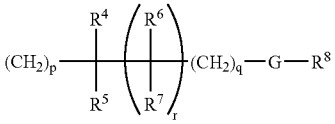 |
| 48 | 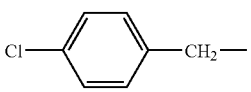 | 2 | 2 | 0 | — | H | 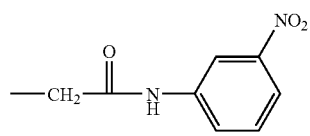 |
| 49 | 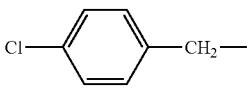 | 2 | 2 | 0 | — | H | 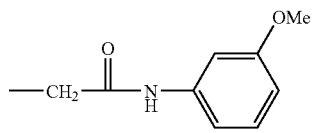 |
| 50 | 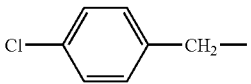 | 2 | 2 | 0 | — | H | 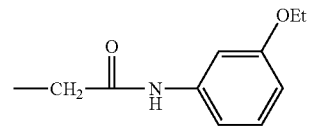 |
| 51 | 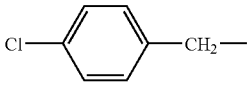 | 2 | 2 | 0 | — | H | 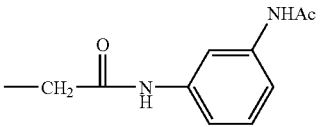 |
| 52 | 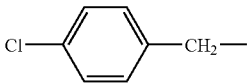 | 2 | 2 | 0 | — | H | 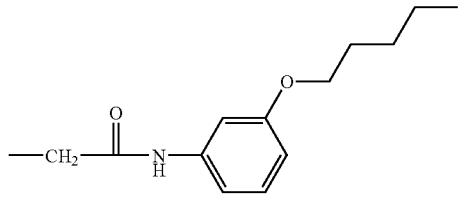 |
| 53 | 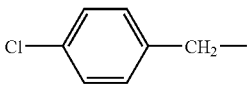 | 2 | 2 | 0 | — | H | 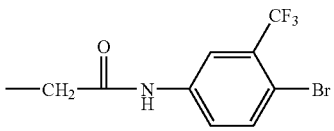 |
| 54 | 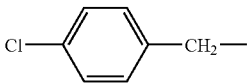 | 2 | 2 | 0 | — | H | 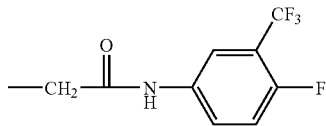 |

The present invention includes the acid addition salt of the cyclic amine compound where such acids include, for example, mineral acids such as hydrochloric acid, hydrobromic acid, sulfuric acid, phosphoric acid, carbonic acid, and the like, as well as organic acids such as citric acid, malic acid, tartaric acid, fumaric acid, methanesulfonic acid, trifluoroacetic acid, formic acid, and the like.

Furthermore, the present invention includes the $C_1$–$C_6$ alkyl addition salt of the cyclic amine compound, such as (N-(2'-Benzamidoethyl)-1-(4-chlorobenzyl)-4-carboxamido-1-methyl-piperidinium iodide), where such alkyl includes, for example, a methyl, ethyl, n-propyl, n-butyl, n-pentyl, n-hexyl, n-heptyl, n-octyl, isopropyl, isobutyl, sec-butyl, tert-butyl, isopentyl, neopentyl, tert-pentyl, 2-methylpentyl, 1-ethylbutyl, and the like, preferably including, a methyl or ethyl group.

The present invention includes racemates or racemic mixtures, and all possible optically active forms of the compounds represented by the above formula (I).

The compounds represented by the above general formula (I) can be synthesized by any of the general preparations given below.

(Preparation I)

A preparation in which one equivalent of a compound represented by the formula (II) below:

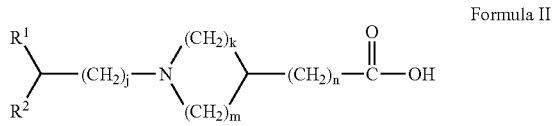

Formula II

{where $R^1$, $R^2$, j, k, m, and n are the same as defined respectively in formula (I)} is reacted with 0.1–10 equivalents of an amine represented by the formula (III) below:

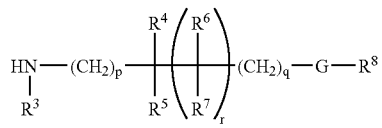

Formula III

{where $R^3$, $R^4$, $R^5$, $R^6$, $R^7$, $R^8$, G, p, q and r are the same as defined respectively in the above formula (I)}, either in the absence or presence of solvent.

Such reactions also can be run by using suitable amounts of a dehydrating agent, such as molecular sieves, coupling reagents, such as dicyclohexylcarbodiimide (DCC), N-ethyl-N'-(3-dimethylaminopropyl)carbodiimide (EDCI or WSC), carbonyldiimidazole (CDI), N-hydroxysuccinimide (HOSu), N-hydroxybenzotriazole (HOBt), benzotriazol-1-yloxytris(pyrrolidino)phosphonium hexafluorophosphate (PyBOP®), 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-(5-norbornene-2,3-dicarboxyimido)-1,1,3,3-tetramethyluronium tetraflouroborate (TNTU), O—N-succinimidyl)-1,1,3,3-tetramethyluronium tetraflouroborate (TSTU), bromotris(pyrrolidino)phosphonium hexafluorophosphate (pyBroP®), and the like, or a base including inorganic salts, such as potassium carbonate, sodium carbonate, sodium hydrogencarbonate, and the like, amines, such as triethylamine, diisopropylethylamine, and pyridine, and the like, or polymer supported bases, such as (piperidinomethyl) polystryene, (morpholinomethyl) polystryene, (diethylaminomethyl) polystryene, poly (4-vinylpyridine), and the like.

(Preparation 2)

A preparation in which one equivalent of an alkylating reagent given by the formula (IV) below:

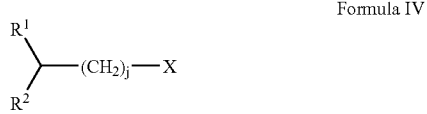

Formula IV

{where $R^1$, $R^2$, and j are the same as defined respectively in formula (I); X represents a halogen atom, alkylsulfonyloxy group, or arylsulfonyloxy group}, is reacted with 0.1–10 equivalents of a compound represented by the formula (V) below:

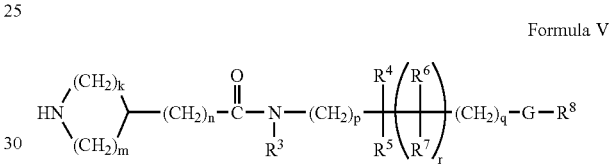

Formula V

{where $R^3$, $R^4$, $R^5$, $R^6$, $R^7$, $R^8$, G, k, m, n, p, q, and r are the same as defined respectively in formula (I)} either in the absence or presence of solvent.

Such reactions also can be run if a base similar to that used in the above preparation 1 is present. In addition, these reactions also can be promoted by iodide, such as potassium iodide, sodium iodide, and the like.

In formula (IV), X represents a halogen atom, alkylsulfonyloxy group, arylsulfonyloxy group. Such halogen atoms include preferably chlorine, bromine, and iodine atoms. Suitable preferred examples for the alkylsulfonyloxy group include methylsulfonyloxy, trifluoromethylsulfonyloxy groups, and the like. A preferred example for the arylsulfonyloxy group is a tosyloxy group.

(Preparation 3)

A preparation in which one equivalent of a compound represented by the formula (VI) below:

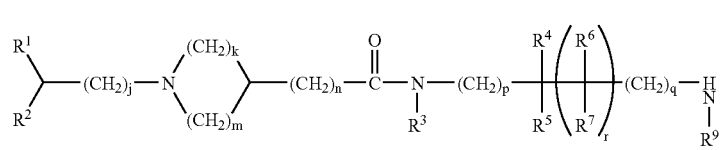

Formula VI

{where $R^1$, $R^2$, $R^3$, $R^4$, $R^5$, $R^6$, $R^7$, $R^8$, j, k, m, n, p, q, and r are the same as defined respectively in formula (I)} is reacted with 0.1–1-equivalents of a carboxylic acid or sulfonic acid represented by the formula (VII) below:

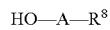

Formula VII

{where R[8] is the same as defined in formula (I); and "A" represents a carbonyl group or sulfonyl group}, or its reactive derivative, either in the absence or presence of solvent.

The reactive derivative for the carboxylic acid or sulfonic acid in the above formula (VII) includes highly reactive carboxylic acid or sulfonic acid derivatives, which are usually used in synthetic organic chemistry, such as acid halides, acid anhydrides, or mixed acid anhydrides.

Such reactions also can be run by using suitable amounts of a dehydrating agent, coupling reagent, or base which are similar to those used in preparation 1.

(Preparation 4)

A preparation in which one equivalent of a compound represented by the above formula (VI) is reacted with 0.1–10 equivalents of a isocyanate or isothiocyanate represented by the formula (VIII) below:

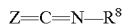
Formula VIII

{where R[8] is the same as defined in formula (I); and "Z" represents a oxygen atom or sulfur atom}, either in the absence or presence of solvent.

(Preparation 5)

A preparation in which one equivalent of a compound represented by the formula (IX) below:

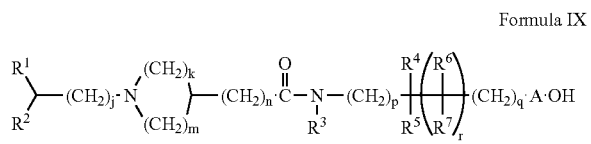
Formula IX

{where R[1], R[2], R[3], R[4], R[5], R[6], R[7], j, k, m, n, p, q, and r are the same as defined respectively in formula (I); and "A" represents a carbonyl group or sulfonyl group} is reacted with 0.1–10 equivalents of an amine represented by the formula (X) below:

Formula X

{where R[8] is the same as defined in formula (I)}, either in the absence or presence of solvent.

Such reactions can be run by using suitable amounts of a dehydrating agent, coupling reagent, or base which are similar to those used in the above preparations.

If the substrates used in any of the preparations contains a substituent that reacts under each reaction condition or is thought to adversely affect the reaction in general, that functional group can be protected by a known suitable protecting group followed by the reaction of the above preparations and deprotection using a known procedure to obtain the desired compound.

Each of the above preparations may use solvents during the reaction, such as halogenated hydrocarbons, such as dichloromethane, chloroform, and the like, aromatic hydrocarbons, such as benzene, toluene, and the like, ethers such as diethyl ether, tetrahydrofuran, and the like, esters, such as ethyl acetate, aprotic polar solvents, such as dimethylformamide, dimethyl sulfoxide, acetontrile, and the like, alcohols, such as methanol, ethanol, isopropyl alcohol, and the like.

The reaction temperature in the preparations should be from about −78° C. to about +150° C., preferably about 0° C. to about 100° C. After completion of the reaction, the usual isolation and purification operations such as concentration, extraction, solid-phase extraction, recrystallization, chromatography, and the like may be used, to isolate the desired cyclic amine compound represented by formula (I). These can be converted into pharmaceutically acceptable acid addition salts or $C_1$–$C_6$ alkyl addition salts by the usual methods.

EXAMPLE A

Preparation of Sodium-(4-chlorobenzyl)isonipecotate

A solution of 4-chlorobenzyl chloride (11.3 g, 70 mmol) and ethyl isonipecotate (10 g, 63.6 mmol) in EtOH (200 mL) was treated with $^iPr_2NEt$ (14.4 mL, 82.7 mmol). The reaction was heated to reflux for 16 h. After cooling to room temperature, the solvent was removed by rotary evaporation. The residue was dissolved in EtOAc (200 mL), washed 3× with 5%. aq. $NaHCO_3$ solution (3×75 mL) and dried over $MgSO_4$. Evaporation of the solvent afforded the desired product (13.5 g, 75%) which was used without further purification. $^1H$ NMR ($CD_3OD$, 300 MHz) δ 1.20 (t, J=7.1 Hz, 3H), 1.66 (m, 2H), 1.84 (m, 2H), 2.04 (m, 2H), 2.30 (m, 1H), 2.80 (m, 2H), 3.46 (s, 2H), 4.07 (q, J=7.1 Hz, 2H), and 7.57 (s, 4H).

A solution of ethyl 1-(4-chlorobenzyl)isonipecotate (1.0 g, 3.6 mmol) in 4:1 dioxane-methanol (16 mL) was treated with 4N aqueous NaOH solution (0.91 mL, 1 equiv). The reaction mixture was heated to 40° C. for 2 hr., before cooling to room temperature. Solvent removal afforded the desired material (1.0 g, quant.) which was used without further purification.

EXAMPLE B

Preparation of N-(2-aminoethyl) 1-(4-chlorobenzyl)isonipecotamide

A solution of sodium 1-(4-chlorobenzyl)isonipecotate (1.0 g, 3.6 mmol) and mono-tert-butyl butyloxycarbonyl-ethylene diamine (527 mg. 3.3 mmol) in $CH_2Cl_2$ (50 mL) was treated with 3-ethyl-1-(3-dimethylaminopropyl)carbodiimide hydrochloride (EDCI) (763 mg, 3.98 mmol) and 1-hydroxybenzotriazole (HOBt) (538 mg, 3.98 mmol). The reaction mixture was stirred at 25° C. for 16 hr. After the reaction was complete by TLC, $CH_2Cl_2$ (50 mL) was added, the organic phase was washed with 2 N aqueous NaOH solution (3×50 mL), sat. aqueous NaCl solution (1×50 mL), sat. aqueous NaCl solution (1×50 mL) and dried over $MgSO_4$. Removal of the solvent afforded the desired material which was used without further purification (1.37 g, 96%). The purity was assessed by RPLC/MS (>90%) ESI/MS m/e 395 ($M^+$+H, $C_{20}H_{30}ClN_3O_3$) (Compound 26).

N-(2 (N'-tert-butyloxycarbonylaminoethyl))-1-(4-chlorobenzyl)isonipecotamide (1.36 g 3.4 mmol) was dissolved in $CH_2Cl_2$ (10 mL), cooled to 0° C. and treated with trifluoroacetic acid (15 mL). After 40 min., the reaction was complete and the solvent was removed by rotary evaporation. The residue was dissolved in 4.1 $tBuOH-H_2O$ (40 mL) and treated with Dowex anion exchange resin until basic. The reaction mixture was filtered and concentrated to afford the desired free amine (965 mg, 95%).

EXAMPLE 1

2'-Benzamidoethyl 1-(4-chlorobenzyl)-piperazine-4-carboxamide

A solution of N-(2-aminoethyl)-1-(4-chlorobenzyl)-isonipecotamide (20 mg, 0.0676 mmol) and benzoic acid (9.9 mg, 0.081 mmol) in $CHCl_3$ (0.5 mL) was treated with EDCI (16 mg, 0.068 mmol), HOBt (11.0 mg, 0.081 mmol) and $Et_3N$ (14 µL, 0.11 mmol). The resulting mixture was stirred at room temperature overnight. The solvent was evaporated and the residue was taken up in $CH_3CN$ (1 mL) at which point the product crystallized from the solution. The solid was filtered and washed with $CH_3CN$ (1 mL) to afford the desired product (13.3 mg, 38%). ESI/MS (m/e) 399.0 ($M^+$+H, $C_{22}H_{26}Cl\,N_3O_2$).

EXAMPLES 2–24

The compounds of this invention were synthesized pursuant to the methods of Example 1 using the corresponding reactants. The ESI/MS data and yields are summarized in Table 2.

TABLE 2

| | Compound No. | Molecular Formula | ESI/MS m/e | Yield (mg) | Yield (%) |
|---|---|---|---|---|---|
| Example 2 | 2 | $C_{23}H_{25}ClF_3N_3O_2$ | 467 | 9.3 | 24 |
| Example 3 | 3 | $C_{23}H_{28}ClN_3O_2$ | 413 | 13.6 | 38 |
| Example 4 | 4 | $C_{23}H_{28}ClN_3O_4S$ | 477 | 7.5 | 19 |
| Example 5 | 5 | $C_{22}H_{25}BrClN_3O_2$ | 476 | 8.3 | 21 |
| Example 6 | 6 | $C_{22}H_{25}Cl_2N_3O_2$ | 433 | 8.7 | 24 |
| Example 7 | 7 | $C_{23}H_{28}ClN_3O_3$ | 429 | 15.1 | 41 |
| Example 8 | 8 | $C_{22}H_{25}ClN_4O_4$ | 444 | 11.9 | 31 |
| Example 9 | 9 | $C_{24}H_{30}ClN_3O_3$ | 443 | 16.2 | 43 |
| Example 10 | 10 | $C_{23}H_{25}ClF_3N_3O_3$ | 483 | 10.5 | 26 |
| Example 11 | 11 | $C_{23}H_{24}ClF_4N_3O_2$ | 485 | 8.9 | 22 |
| Example 12 | 12 | $C_{23}H_{24}ClF_4N_3O_2$ | 485 | 10.2 | 25 |
| Example 13 | 13 | $C_{24}H_{27}ClN_4O_2$ | 438 | 8.1 | 22 |
| Example 14 | 14 | $C_{21}H_{26}ClN_3O_2S_2$ | 451 | 16.2 | 42 |
| Example 15 | 15 | $C_{23}H_{25}ClF_3N_3O_2$ | 485 | 11.4 | 29 |
| Example 16 | 16 | $C_{24}H_{30}ClN_3O_4$ | 459 | 8.7 | 22 |
| Example 17 | 17 | $C_{25}H_{34}CN_3O_3$ | 459 | 7 | 18 |
| Example 18 | 18 | $C_{27}H_{30}ClN_3O_3$ | 479 | 18.8 | 47 |
| Example 19 | 19 | $C_{22}H_{25}ClF_3N_3O_3$ | 471 | 9.3 | 23 |
| Example 20 | 20 | $C_{22}H_{24}Cl_2N_4O_4$ | 478 | 10 | 25 |
| Example 21 | 21 | $C_{22}H_{25}ClFN_3O_2$ | 417 | 9.1 | 25 |
| Example 22 | 22 | $C_{22}H_{24}Cl_3N_3O_2$ | 467 | 9.6 | 24 |
| Example 23 | 23 | $C_{24}H_{27}ClF_3N_3O_2$ | 481 | 10.8 | 27 |
| Example 24 | 24 | $C_{25}H_{32}ClN_3O_5$ | 489 | 21 | 51 |

EXAMPLE 25

3'phenyl-2'-oxo-ethyl 1-(4-chlorobenzyl)-piperazine 4-carboxamide (Compound 27)

A solution of sodium 1-(4'-chlorobenzyl)-isonipecotate and 2-aminoacetophenone (12 mg, 0.091 mmol) in $CHCl_3$ (0.1 mL) was treated with EDCI (21 mg, 0.11 mmol), HOBt (16 mg, 0.12 mmol) and $^iPr_2NEt$ (19 µL, 0.14 mmol). The reaction mixture was stirred at room temperature for 16 hr. The solvent was evaporated and the product was purified by cation exchange chromatography (32.1 mg, 95%) ESI/MS m/e 370 ($M^+$+H, $C_{21}H_{23}ClN_2O_2$).

EXAMPLES 26–35

The compounds of this invention were synthesized pursuant to methods of Example 25 using the corresponding reactants. The ESI/MS data and yields are summarized in Table 3.

TABLE 3

| | Compound No. | Molecular Formula | ESI/MS m/e | Yield (mg) | Yield (%) |
|---|---|---|---|---|---|
| Example 26 | 28 | $C_{21}H_{22}BrClN_2O_2$ | 448 | 38.5 | 94 |
| Example 27 | 29 | $C_{23}H_{27}ClN_2O_4$ | 430 | 37.2 | 95 |
| Example 28 | 30 | $C_{28}H_{27}ClN_2O_4$ | 490 | 36.3 | 96 |
| Example 29 | 31 | $C_{22}H_{25}ClN_2O_3$ | 416 | 41.8 | 94 |
| Example 30 | 32 | $C_{21}H_{22}Cl_2N_2O_2$ | 404 | 5.5 | 15 |
| Example 31 | 33 | $C_{21}H_{22}BrClN_2O_2$ | 448 | 15.2 | 37 |
| Example 32 | 34 | $C_{21}H_{22}ClFN_2O_2$ | 388 | 9.4 | 27 |
| Example 33 | 35 | $C_{21}H_{21}Cl_3N_2O_2$ | 438 | 1.4 | 3 |
| Example 34 | 36 | $C_{21}H_{24}ClN_3O_2$ | 385 | 6.4 | 21 |
| Example 35 | 54 | $C_{21}H_{22}ClN_3O_4$ | 415 | 19.7 | 26 |

EXAMPLE 36

N-1-(4-Chlorobenzyl)-piperazine-4-carboxamido-glycine methyl ester (Compound 25)

A solution of sodium 1-(4-chlorobenzyl)-isonipecotate (1 g, 3.63 mmol) in $CH_2Cl_2$ (100 mL) was treated with glycine methyl ester hydrochloride (0.50 g, 3.99 mmol), EDCl (834 mg, 4.35 mmol), HOBt (588 mg, 4.35 mmol) and $Et_3N$ (0.5 mL, 4.0 mmol). The reaction mixture was stirred at room temperature for 16 hr. After the reaction was complete, the organic phase was washed with $H_2O$ (3×50 mL), dried ($MgSO_4$) and concentrated. The resulting material was purified via column chromatography ($SiO_2$, 3% $CH_3OH$—$CH_2Cl_2$) to afford the desired material as a yellow solid (929 mg, 79%), ESI/MS m/e 395 ($M^+$+H, $C_{20}H_{30}ClN_3O_3$).

EXAMPLE C

Sodium N-(1-(4-chlorobenzyl)-piperazine-4-carboxamido)glycinate

A solution of N-(1-(4-chlorobenzyl)-piperazine-4-carboxamido) glycine methyl ester (813 mg, 2.50 mmol) in dioxane-$CH_3OH$ (3:1, 12 mL) was treated with 4N aqueous NaOH solution (0.63 mL, 1 equiv.). The mixture was stirred at room temperature for 2 hours. Solvent removal afforded the desired material which was used without further purification (885 mg, 100%).

EXAMPLE 37

N-(1-(4-Chlorobenzyl)-piperazine-4-carboxamido) glycine benzamide (Compound 36)

Sodium N-(1-(4-chlorobenzyl)-piperazine-4-carboxamido)glycinate (20 mg, 0.060 mmol) and aniline (6.2 mg, 0.66 mmol) were dissolved in $CHCl_3$ (1 mL). HBTU (25 mg, 0.066), HOBt (8.1 mg, 0.066 mmol) and $Et_3N$ (17 µL, 0.12 mmol) were added and the reaction mixture was stirred for 16 hr. The solvent was removed and the compound was dissolved into $CH_2Cl_2$ (2 mL). The organic layer was washed with 2N aqueous NaOH solution (2N mL), brine (1×1 mL) and concentrated. Purification via RPLC/MS afforded the desired material (6.4 mg, 21%). ESI/MS 385 ($M^+$+H, $C_{26}H_{24}ClN_3O_2$).

EXAMPLES 38–54

The compounds of this invention were synthesized pursuant to methods of Example 37 using the corresponding reactant respectively. The ESI/MS data and yields are summarized in Table 4.

TABLE 4

| | Compound No. | Molecular Formula | ESI/MS m/e | Yield (mg) | Yield (%) |
|---|---|---|---|---|---|
| Example 38 | 37 | $C_{22}H_{23}ClF_3N_3O_2$ | 453 | 2.9 | 9 |
| Example 39 | 38 | $C_{22}H_{23}ClN_3O_2$ | 410 | 4.9 | 16 |
| Example 40 | 39 | $C_{23}H_{26}ClN_3O_3$ | 427 | 10.2 | 31 |
| Example 41 | 40 | $C_{22}H_{23}ClF_3N_3O_2$ | 453 | 7 | 21 |
| Example 42 | 41 | $C_{23}H_{28}ClN_3O_2$ | 413 | 18 | 57 |
| Example 43 | 42 | $C_{22}H_{25}ClN_4O_3$ | 428 | 5.1 | 16 |
| Example 44 | 43 | $C_{25}H_{32}ClN_3O_2$ | 441 | 17.2 | 51 |
| Example 45 | 44 | $C_{21}H_{23}BrClN_3O_2$ | 463 | 7.2 | 21 |
| Example 46 | 45 | $C_{21}H_{23}ClFN_3O_2$ | 403 | 7.5 | 24 |
| Example 47 | 46 | $C_{21}H_{23}Cl_2N_3O_2$ | 419 | 4.7 | 15 |
| Example 48 | 47 | $C_{21}H_{23}ClN_4O_4$ | 430 | 5.9 | 18 |
| Example 49 | 48 | $C_{22}H_{26}ClN_3O_3$ | 415 | 16 | 50 |
| Example 50 | 49 | $C_{23}H_{28}ClN_3O_3$ | 429 | 10.3 | 31 |
| Example 51 | 50 | $C_{23}H_{27}ClN_4O_3$ | 442 | 10.3 | 30 |
| Example 52 | 51 | $C_{26}H_{34}ClN_3O_3$ | 471 | 15.3 | 43 |
| Example 53 | 52 | $C_{22}H_{22}BrClF_3N_3O$ | 531 | 5.4 | 14 |
| Example 54 | 53 | $C_{22}H_{22}ClF_4N_3O_2$ | 471 | 11.5 | 33 |

EXAMPLE (55)

Measurement of Inhibition of MIP-1α Binding to THP-1 Cells by Test Compounds Human monocytic leukemia cell line THP-1 was suspended in assay buffer (RPMI-1640(Gibco-BRL Co.) containing 0.1% BSA and 25 mM HEPES adjusted to pH 7.4) to give a cell suspension of a concentration of 1×10⁷ cells/mL. The test compound was diluted in the assay buffer and used as the test compound solution. Iodinated human MIP-1α (Dupont NEN Co.) was diluted in assay buffer to 250 nCi/mL and used as the labeled ligand solution. In a 96 well filter plate (Millipore Co.), 25 μL of test compound solution, 25 μL of labeled ligand solution and 50 μL of cell suspension were aliquoted into each well in this order, stirred (total reaction volume 100 μL), and incubated for one hour at 18° C.

After the reaction, the reaction solution was filtered, and the filter was washed twice with 200 μL of cold PBS (200 μL of cold PBS was added and then filtered). The filter was air-dried and 25 μL of liquid scintillator was added into each well. The radioactivity retained by the cells on the filter were measured using TopCount (Packard Instrument Co.).

To calculate the ability of test compounds to inhibit binding of human MIP-1α to THP-1 cells, non-specific binding determined by adding 100 ng of unlabeled human MIP-1 α (Peprotech Co.) in place of the test compound was subtracted, while the counts with no test compound added were taken as 100%.

Inhibition (%)={1−(A−B)/(C−B)}×100

(A, counts with test compound added; B, counts with 100 ng of unlabeled human MIP-1 α added; counts with [$^{125}$I]-labeled human MIP-1 α added).

When inhibition by the cyclic amine derivatives of this invention were measured, for example, the following compounds demonstrated 50%–80% and >80% inhibitory activity at 10 μM, respectively.

These compounds are 50%–80% inhibition at 10 μM: Compound Nos. 1, 3, 4, 8, 14, 18, 21, 23, 27, 32, 33, 34, 35, 36, 39, 40, 41, 44, 45, 46, 47, 48, 49, and 52. These compounds are >80% inhibition at 10 μM: compound Nos. 2, 5, 6, 7, 9, 10, 11, 12, 13, 15, 16, 17, 19, 20, 22, and 24.

All publications and patent documents cited herein are incorporated by reference in their entirety for all purposes.

What is claimed is:

1. A compound of the formula (I):

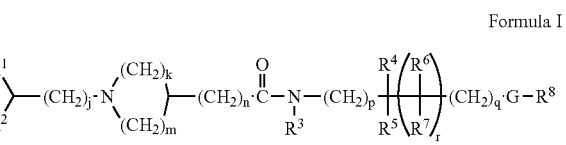

Formula I a pharmaceutically acceptable acid addition salt thereof or a pharmaceutically acceptable $C_1$–$C_6$ alkyl addition salt thereof, wherein $R^1$ is a phenyl group, a $C_3$–$C_8$ cycloalkyl group, or a combination thereof, in which the phenyl group may be condensed with a benzene ring to form a condensed ring, and the phenyl group, $C_3$–$C_8$ cycloalkyl group, or condensed may be substituted with one or mare of a halogen atom, a hydroxy group, a cyano group, a nitro group, a carboxy group, a carbamoyl group, a $C_1$–$C_6$ alkyl group, a $C_3$–$C_8$ group, a $C_2$–$C_6$ alkenyl group, a $C_1$–$C_6$ alkoxy group, a $C_1$–$C_6$ alkylthio group, $C_3$–$C_5$ alkylene group, a $C_2$–$C_4$ alkylenoxy group, a $C_1$–$C_3$ alkylenedioxy group, a phenyl group, a phenoxy group, a phenylthio group, a benzyl group, a benzyloxy group, a benzoylamino group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_4$–$C_9$ N-cycloalkylcarbonyl group, a $C_1$–$C_6$ alkylsulfonyl group, a $C_3$–$C_8$ (alkoxycarbonyl) methyl group, a N-phenylcarbamoyl group, a piperidinocarbonyl group, a morpholinocarbonyl group, a 1-pyrrolidinylcarbonyl group, an amino group, a mono ($C_1$–$C_6$ alkyl)amino group, or a di($C_1$–$C_6$ alkyl)amino group, $R^2$ is a hydrogen atom, a $C_1$–$C_6$ alkyl group, a $C_2$–$C_7$ alkoxycarbonyl group, a hydroxy group, or a phenyl group, in which the $C_1$–$C_6$ alkyl or phenyl group may be substituted with one or more of a halogen atom, a hydroxy group, a $C_1$–$C_6$ alkyl group, or a $C_1$–$C_6$ alkoxy group, and when j=0, $R^2$ is not a hydroxy group;

j represents an integer of 0;

k represents an integer of 2;

m represents an integer of 2, provided the sum of k and m is 4;

n represents an integer of 0;

$R^3$ is a hydrogen atom or a $C_1$–$C_6$ alkyl group optionally substituted with one or two phenyl groups each of which may be substituted with one or more of a halogen atom, a hydroxy group, a $C_1$–$C_6$ alkyl group, or a $C_1$–$C_6$ alkoxy group;

$R^4$ and $R^5$ are the same or different from each other and are a hydrogen atom, a hydroxy group, or a $C_1$–$C_6$ alkyl group, in which the $C_1$–$C_6$ alkyl group is optionally substituted with one or more of a halogen atom, a hydroxy group, a cyano group, a nitro group, a carboxy group, a carbamoyl group, a mercapto group, a guanidino group, a $C_3$–$C_8$ cycloalkyl group, a $C_1$–$C_6$ alkoxy group, a $C_1$–$C_6$ alkylthio group; a phenyl group optionally substituted with one or more of a halogen atom, a hydroxy group, a $C_1$–$C_6$ alkyl group, or a $C_1$–$C_6$ alkoxy group; a phenoxy group, a benzyloxy group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_1$–$C_6$ alkylsulfonyl group, an amino group, a mono($C_1$–$C_6$ alkyl)amino group, a di($C_1$–$C_6$ alkyl)amino group, or an aromatic heterocyclic group having 1–3 of heteroatoms selected from the group consisting of an oxygen atom, a sulfur atom, and a nitrogen atom, or a combination thereof, or $R^4$ and $R^5$ taken together form a 3 to 6 membered cyclic hydrocarbon;

$R_6$ and $R_7$ are the same or different from each other and are a hydrogen atom, a hydroxy group, or a $C_1$–$C_6$ alkyl group, in which the $C_1$–$C_6$ alkyl group is optionally substituted with one or more of a halogen atom, a hydroxy group, a cyano group, a nitro group, a carboxy group, a carbamoyl group, a mercapto group, a guanidino group, a $C_3$–$C_8$ cycloalkyl group, a $C_1$–$C_5$ alkoxy group, a $C_1$–$C_6$ alkylthio group; a phenyl group optionally substituted with one or more of a halogen atom, a hydroxy group, a $C_1$–$C_6$ alkyl group, or a $C_1$–$C_6$ alkoxy group; a phenoxy group, a benzyloxy group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_1$–$C_6$ alkylsulfonyl group, an amino group, a mono($C_1$–$C_6$ alkyl)amino group, or a di($C_1$–$C_6$ alkyl)amino group;

p represents an integer of 0–1;

q represents an integer of 0–1;

r represents an integer of 0–1;

G is a group represented by —CO—, —$SO_2$—, —CO—O—, —$NR^9$—CO—, —CO—$NR^9$—, —NH—CO—NH—, —NH—CS—NH—, —$NR^9$—$SO_2$—, —$SO_2$—$NR^9$—, —NH—CO—O—, or —O—CO—NH—, wherein $R^9$ is a hydrogen atom or a $C_1$–$C_6$ alkyl group, or $R^9$ taken together with $R^7$ represents $C_2$–$C_5$ alkylene group;

$R^8$ is a phenyl group, a $C_3$–$C_8$ cycloalkyl group, a $C_1$–$C_6$ alkoxy group, a $C_3$–$C_8$ cycloalkenyl group, a benzyl group, or an aromatic heterocyclic group having 1–3 heteroatoms selected from the group consisting of an oxygen atom, a sulfur atom, and a nitrogen atom, or a combination thereof, in which the phenyl, benzyl, or aromatic heterocyclic group may be condensed with a benzene ring or an aromatic heterocyclic group having 1–3 heteroatoms selected from the group consisting of an oxygen atom, a sulfur atom, and a nitrogen atom, or a combination thereof, to form a condensed ring, and the phenyl group, $C_3$–$C_8$ cycloalkyl group, $C_3$–$C_8$ cycloalkyl group, benzyl group, aromatic heterocyclic group, or condensed ring may be substituted with one or more of a halogen atom, a hydroxy group, a mercapto group, a cyano group, a nitro group, a thiocyanato group, a carboxy group, an amido group, a carbamoyl group, a trifluoromethyl group, a $C_1$–$C_6$ alkyl group, a $C_3$–$C_6$ cycloalkyl group, a $C_2$–$C_6$ alkenyl group, a $C_1$–$C_6$ alkoxy group, a $C_3$–$C_8$ cycloalkyloxy group, a $C_1$–$C_6$ alkylthio group, a $C_1$–$C_3$ alkylenedioxy group, a phenyl group, a phenoxy group, a phenylamino group, a benzyl group, a benzoyl group, a phenylsulfinyl group, a phenylsulfonyl group, a 3-phenylureido group, a $C_2$–$C_7$ alkanoyl group, a $C_2$–$C_7$ alkoxycarbonyl group, a $C_2$–$C_7$ alkanoyloxy group, a benzyloyloxy group, a $C_2$–$C_7$ alkanoylamino group, a $C_2$–$C_7$ N-alkylcarbamoyl group, a $C_1$–$C_6$ alkylsufonyl group, a phenylcarbamoyl group, a N,N-di ($C_1$–$C_6$ alkyl) sulfamoyl group, an amino group, a mono($C_1$–$C_6$ alkyl)amino group, a di($C_1$–$C_6$ alkyl)amino group, a benzylamino group, a $C_2$–$C_7$ (alkoxycarbonyl) amino group, a $C_1$–$C_6$, (alkylsulfonyl) amino group, or a bis ($C_1$–$C_6$ alkylsulfonyl) amino group.

2. The compound of claim 1, or a salt thereof, wherein $R^1$ is a phenyl group substituted with one or more of a halogen atom, a hydroxy group, a $C_1$–$C_6$ alkyl group, a $C_2$–$C_6$ alkoxy group, or an amino group; $R^2$ is a hydrogen atom, j=0, k=2, m=2, n=0, $R^3$ is a hydrogen atom, p=0 or 1, r=0, $R^4$ and $R^5$ are hydrogen atoms, q=0, G is —$NR^9$—CO—, —CO—, or O—CO—NH; and $R^8$ is a $C_1$–$C_6$ alkoxy group, a phenyl group or an aromatic hetercyclic group having 1–3 heteroatoms selected from the group consisting of an oxygen atom, a sulfur atom, and a nitrogen atom, or a combination thereof, in which the phenyl or aromatic heterocyclic group or condensed ring may be substituted with one or more of a halogen atom, a trifluoromethyl group, an amido group, a $C_1$–$C_6$ alkylthio group, a $C_1$–$C_6$ alkoxy group, a nitro group, a phenyl group, a cyano group, a benzoyloxy group, a $C_2$–$C_7$ alkanoyl group, or a $C_2$–$C_7$ alkanoylamino group.

3. A pharmaceutical composition comprising a compound of claim 1, or salt thereof, and a pharmaceutically-acceptable carrier.

4. A method of treating an inflammatory or immunoregulatory disease in a patient in need of such treatment comprising administering to the patient a therapeutically-effective amount of a compound of claim 1 or a salt thereof, wherein the diseases are selected from the group consisting of transplant rejection, atherosclerosis, rheumatoid arthritis, psoriasis, asthma, ulcerative colitis, glomerulonephritis, multiple sclerosis, pulmonary fibrosis, and myocarditis.

5. A method of treating human immunodeficiency virus in a patient in need of such treatment comprising administering to the patient a therapeutically-effective amount of a compound of claim 1 or a salt thereof.

6. A pharmaceutical composition comprising a compound of claim 2, or salt thereof, and a pharmaceutically-acceptable carrier.

7. A method of treating an inflammatory or immunoregulatory disease in a patient in need of such treatment comprising administering to the patient a therapeutically-effective amount of a compound of claim 2 or a salt thereof, wherein the diseases are selected from the group consisting of transplant rejection, atherosclerosis, rheumatoid arthritis, psoriasis, asthma, ulcerative colitis, glomerulonephritis, multiple sclerosis, pulmonary fibrosis, and myocarditis.

8. A method of treating human immunodeficiency virus in a patient in need of such treatment comprising administering to the patient a therapeutically-effective amount of a compound of claim 2 or a salt thereof.

* * * * *

UNITED STATES PATENT AND TRADEMARK OFFICE
CERTIFICATE OF CORRECTION

PATENT NO. : 7,125,895 B1
APPLICATION NO. : 09/569766
DATED : October 24, 2006
INVENTOR(S) : Tarby et al.

It is certified that error appears in the above-identified patent and that said Letters Patent is hereby corrected as shown below:

In Column 36, Line 25:
"$C_3$-$C_8$ cycloalkyl group, or condensed may be substi-"

Should read: -- $C_3$-$C_8$ cycloalkyl group, or condensed ring may be substi- --

In Column 37, Line 52:
"cycloalkyl group, benzyl group, aromatic heterocyclic"

Should read: -- cycloalkenyl group, benzyl group, aromatic heterocyclic --

Signed and Sealed this

Fifth Day of August, 2008

JON W. DUDAS
*Director of the United States Patent and Trademark Office*